US008097608B2

(12) United States Patent
Youdim et al.

(10) Patent No.: US 8,097,608 B2
(45) Date of Patent: Jan. 17, 2012

(54) METHODS FOR TREATMENT OF CARDIOVASCULAR DISORDERS AND DISEASES

(75) Inventors: Moussa B. H. Youdim, Haifa (IL); Ofer Binah, Nofit (IL); Zaid A. Abassi, Haifa (IL); Yaron Barac, Kiryat Motzkin (IL)

(73) Assignees: Technion Research and Development Foundation Ltd., Haifa (IL); Rappaport Family Institute, Haifa (IL)

( * ) Notice: Subject to any disclaimer, the term of this patent is extended or adjusted under 35 U.S.C. 154(b) by 519 days.

(21) Appl. No.: 11/449,862

(22) Filed: Jun. 9, 2006

(65) Prior Publication Data

US 2006/0287401 A1    Dec. 21, 2006

Related U.S. Application Data

(63) Continuation-in-part of application No. 10/952,367, filed on Sep. 29, 2004, now abandoned.

(60) Provisional application No. 60/524,616, filed on Nov. 25, 2003, provisional application No. 60/570,496, filed on May 13, 2004.

(51) Int. Cl.
*A61K 31/135* (2006.01)
(52) U.S. Cl. ........................................ 514/183; 514/657
(58) Field of Classification Search .................... 514/657
See application file for complete search history.

(56) References Cited

U.S. PATENT DOCUMENTS

| | | | |
|---|---|---|---|
| 3,297,527 A | 1/1967 | Elslager |
| 4,861,800 A | 8/1989 | Buyske |
| 5,151,419 A | 9/1992 | Perenyi et al. |
| 5,151,449 A | 9/1992 | Milgram |
| 5,169,868 A | 12/1992 | Yu et al. |
| 5,192,808 A | 3/1993 | Ruehl et al. |
| 5,225,446 A | 7/1993 | Milgram |
| 5,242,950 A | 9/1993 | Fries Hastings |
| 5,276,057 A | 1/1994 | Milgram et al. |
| 5,387,612 A | 2/1995 | Youdim et al. |
| 5,387,615 A | 2/1995 | Milgram et al. |
| 5,453,446 A | 9/1995 | Youdim et al. |
| 5,457,133 A | 10/1995 | Youdim et al. |
| 5,486,541 A | 1/1996 | Sterling et al. |
| 5,519,061 A | 5/1996 | Youdim et al. |
| 5,532,415 A | 7/1996 | Youdim et al. |
| 5,576,353 A | 11/1996 | Youdim et al. |
| 5,599,991 A | 2/1997 | Youdim et al. |
| 5,639,913 A | 6/1997 | Lidor et al. |
| 5,668,181 A | 9/1997 | Youdim et al. |
| 5,744,500 A | 4/1998 | Youdim et al. |
| 5,786,390 A | 7/1998 | Youdim et al. |
| 5,840,979 A | 11/1998 | Durden et al. |
| 5,891,923 A | 4/1999 | Youdim et al. |
| 6,251,938 B1 | 6/2001 | Chorev et al. |
| 6,251,950 B1 | 6/2001 | Durden et al. |
| 6,277,886 B1 | 8/2001 | Levy et al. |
| 6,303,650 B1 | 10/2001 | Chorev et al. |
| 6,316,504 B1 | 11/2001 | Youdim et al. |
| 6,395,780 B1 | 5/2002 | Arlt et al. |
| 6,462,222 B1 | 10/2002 | Chorev et al. |
| 6,538,025 B2 | 3/2003 | Chorev et al. |
| 6,562,365 B2 | 5/2003 | Blume et al. |
| 6,630,514 B2 | 10/2003 | Youdim et al. |
| 2002/0019421 A1 | 2/2002 | Biberman |
| 2002/0064552 A1 | 5/2002 | Blume et al. |
| 2002/0137786 A1 | 9/2002 | Tatton et al. |
| 2002/0188020 A1 | 12/2002 | Chorev et al. |

FOREIGN PATENT DOCUMENTS

| | | |
|---|---|---|
| EP | 0538134 A2 | 4/1993 |
| WO | 9826775 A1 | 6/1998 |
| WO | 9827055 A1 | 6/1998 |

OTHER PUBLICATIONS

Nwogu et al. (Circulation. 2001;104:2216-21).*
Eliash et al. (J Neural Transm. 2001;108:909-23).*
Betkowski et al. (Current Opinion in Cardiology (2000);15:293-303).*
Klabunde, Richard, PhD (CV Pharmacology: Myocardial Infarction—Causes, Effects: Cardiovascular Pharmacology Concepts. Mar. 2007; retrieved from URL: http://www.cvpharmacology.com/clinical%20topics/myocardial%20infarction.htm).*
S. Eliash et al., "Rasagiline and its (S) enantiomer increase survival and prevent stroke in salt-loaded stroke-prone spontaneously hypertensive rats", Journal of Neural Transmission (2001) 108: 909-923.
K. Kitsis et al., "Introduction—cell death in heart failure", Heart Fail Rev 13:107-109 (2008).
P. Kossmehl et al., "Mechanisms of apoptosis after ischemia and reperfusion: Role of the renin-angiotensin system", Apoptosis 11: 347-358 2006.
Sun., "Myocardial repair/remodelling following infarction: roles of local factors", Cardiovascular Research 81, 482-490 (2009).
Tiyyagura et al., "Left Ventricular Remodeling after Myocardial Infarction: Past, Present, and Future", The Mount Sinai Journal of Medicine vol. 73 No. 6, pp. 840-851 (2006).
Takemura et al., "Role of apoptosis in remodeling after myocardial infarction" (Science Direct) Pharmacology & Therapeutics 104 1-16 (2004).
Abbate et al., "Pathophysiologic Role of Myocardial Apoptosis in Post-Infarction Left Ventricular Remodeling" Journal of Cellular Physiology 193:145-153 (2002).
Abassi et al., "Cardiovascular activity of rasagiline, a selective and potent inhibitor of mitochondrial monoamine oxidase B: comparison with selegiline" British Journal of Pharmacology 143:371:378 (2004).
Ryan et al., "1999 Update: ACC/AHA Guidelines for the Management of Patients With Acute Myocardial Infarction: Executive Summary and Recommendations: A Report of the American College of Cardiology/American Heart Association Task Force on Practice Guidelines (Committee on Management of Acute Myocardial Infarction)" Circulation 100:1016-1030 (1999).

(Continued)

*Primary Examiner* — Frederick Krass
*Assistant Examiner* — Chris Simmons
(74) *Attorney, Agent, or Firm* — Browdy and Neimark, PLLC

(57) ABSTRACT

Propargylamine, propargylamine derivatives including N-propargyl-1-aminoindan, enantiomers and analogs thereof, and pharmaceutically acceptable salts thereof, are useful for prevention or treatment of cardiovascular disorders, diseases and conditions.

5 Claims, 15 Drawing Sheets

OTHER PUBLICATIONS

Antman et al., "ACC/AHA Guidelines for the Management of Patients With ST-Elevation Myocardial Infarction-Executive Summary: A Report of the American College of Cardiology/American Heart Association Task Force on Practice Guidelines (Writing Committee to Revise the 1999 Guidelines for the Management of Patients With Acute Myocardial Infarction)" J. Am Coll Cardiol., 44: 671-719 (2004).

S.B. King III et al., "2007 Focused Update of the ACC/AHA/SCAI 2005 Guideline Update for Percutaneous Coronary Intervention A Report of the American College of Cardiology/American Heart AssociationTask Force on Practice Guidelines: 2007 Writing Group to Review New Evidence and Update the ACC/AHA/SCAI 2005 Guideline Update for Percutaneous Coronary Intervention, Writing on Behalf of the 2005 Writing Committee" Circulation 117:261-295 (2008).

Bar-Am et al., "Contrasting neuroprotective and neurotoxic actions of respective metabolites of anti-Parkinson drugs rasagiline and selegiline" Neuroscience Letters 355:169-172 (2004).

Shite et al., "Selegiline improves cardiac sympathetic terminal function and b-adrenergic responsiveness in heart failure", Am J. Physiol Heart Circ Physiol, 279: H1283-H1290 (2000).

Speiser et al., "Studies with rasagiline, a MAO-B inhibitor, in experimental focal ischemia in the rat", J Neural Transm, 106:593-606 (1999).

Weinreb et al., "Neuroprotection via pro-survival protein kinase C isoforms associated with Bcl-2 family members", The FASEB Journal express, article 10.1096 (2004).

Van de Werf et al., "Acute Myocardial Infarction (AMI) 2003", ESC Guidelines Desk Reference, ESC Committee for Practice Guidelines to Improve the quality of clinical practice and patient care in Europe, Cardiovascular Medicine, Compendium of Abridged ESC Guidelines, European Society of Cardiology, (2008), pp. 69-75.

Fuentes et al., "Central Mediation of the Antihypertensive Effect of Pargyline in Spontaneously Hypertensive Rats", European Journal of Pharmacology 57:21-27 (1979).

Fukasawa et al., "The Central Mechanism of the Hypotensive Effects of CLOkGYLINE and DEPkENYL in Spontaneously Hypertensive Rats", Biogenic Amines, vol. 6. No. 6. pp. 549-557 (1989).

Hubalek et al.,"Inactivation of Purified Human Recombinant Monoamine Oxidases A and B by Rasagiline and Its Analogues", J. Med. Chem. 47:1760-1766 (2004).

Huebner et al., N-Methyl-N-2-propynyl-1-indanamine. A Potent Monoamine Oxidase Inhibitor' Journal of Medicinal Chemistry, 9, 830-832 (1966).

Kang et al., "Apoptosis and Heart Failure A Critical Review of the Literature", Kang et al., Circulation Research, 86, 1107-1113 (2000).

Kovelman et al., "Molecular-Biological Problems of the Creation of Drugs and Study of the Mechanism of Their Action Structure and Activity of Irreversible Inhibitors of Monoamine Oxidase", Pharmaceutical Chemistry Journal, 24:379-390 (1990).

Maruyama et al., "The anti-parkinson drug, rasagiline, prevents apoptotic DNA damage induced by peroxynitrite in human dopaminergic neuroblastoma SH-SY5Y cells", J Neural Transm, 109: 467-481 (2002).

Matyus et al., "Semicarbazide-Sensitive Amine Oxidase: Current Status and Perspectives" Current Medicinal Chemistry, 2005, 11, 1285-1298.pdf.

Yogev-Falach et al., "The involvement of mitogen-activated protein (MAP) kinase in the regulation of amyloid precursor protein processing by novel cholinesterase inhibitors derived from rasagiline" The FASEB Journal, 16:1674-1676 (2002).

Youdim et al., Molecular Basis of Neuroprotective Activities of Rasagiline and the Anti-Alzheimer Drug TV3326 [(N-Propargyl-(3R)Aminoindan-5-YL)-Ethyl Methyl Carbamate] Cellular and Molecular Neurobiology, 2:555-573 (2001).

Youdim et al., Novel neuroprotective anti-Alzheimer drugs with anti-depressant activity derived from the anti-Parkinson drug, rasagiline, Mechanisms of Ageing and Development 123:1081-1086 (2002).

American Heart Association/American College of Cardiology joint scientific statement, "New guidelines address care, treatment for heart attacks" Journal Report (Dec. 11, 2007).

Ryan et al., "1999 Update: ACC/ANA Guidelines for the Management of Patients With Acute Myocardial Infarction: A Report of the American College of Cardiology/American Heart Association Task Force on Practice Guidelines (Committee on Management of Acute Myocardial Infarction)" J Am Coll Cardiol., 34:890-911 (1999).

S. Abu-Raya et al.,"Neuroprotective and neurotoxic effects of monoamine oxidase-B inhibitors and derived metabolites under ischemia in PC12 cells", European Journal of Pharmacology 434:109-116 (2002).

O. Bar-Am et al., "Contrasting neuroprotective and neurotoxic actions of respective metabolites of anti-Parkinson drugs rasagiline and selegiline", Neuroscience Letters 355:169-172 (2004).

O. Bar-Am et al., "Regulation of Bcl-2 family proteins, neurotrophic factors, and APP processing in the neurorescue activity of propargylamine", The FASEB Journal express article 10.1096: 1-26 (2005).

P. Barter et al., "Effects of Torcetrapib in Patients at High Risk for Coronary Events", The New England Journal of Medicine vol. 357:21 2109-2122 (2007).

W. Birkmayer et al., "The Potentiation of the Anti Akinetic Effect after L-Dopa Treatment by an Inhibitor of Mao-B, Deprenil", Journal of Neural Transmission 36, 303-326 (1975).

Boulton et al., "Aliphatic Propargylamines: New Antiapoptotic Drugs." Drug Development Research 42; 150-156 (1997).

M.J. Chapman., "Therapeutic elevation of HDL-cholesterol to prevent atherosclerosis and coronary heart disease" Pharmacology & Therapeutics 111 893-908 (2006).

A. Churchyard et al., "Selegiline-induced postural hypotension in Parkinson's disease: a longitudinal study on the effects of drug withdrawal", Mov Disord. 14(2):246-251 (1999).

J. P. M. Finberg et al., Chapter 67: Pharmacology of Rasagline (N-Propargyl-1R-Aminoindan); Parkinson's Disease: Advances in Neurology 495-499 (1999).

S. Glezer et al., "Pharmacological comparison between the actions of methamphetamine and 1-aminoindan stereoisomers on sympathetic nervous function in rat vas deferens", European Journal of Pharmacology (2003) 472:173-177.

A.J. Lees , "Comparison of therapeutic effects and mortality data oflevodopa and levodopa combined with selegiline in patients with early, mild Parkinson's disease", BMJ 311:1602-1607 (1995).

A. Levy et al., "Pharmacogenomics in prevention of diabetic cardiovascular disease: utilization of the haptoglobin genotype in determining benefit from vitamin E", Experts Rev. Cardiovasc. Ther. 5(6), 1-7 (2007).

Kitani et al., "Do Antioxidant Strategies Work Against Aging and Age-associated Disorders?, Propargylamines: A Possible Antioxidant Strategy." Annals of the New York Academy of Sciences 928:249-260 (2001).

B. Maron et al., "Contemporary Definitions and Classification of Cardiomyopathies", Journal of the American Heart Association 113; 1807-1816 (2006).

W. Maruyama et al.,"Antiapoptic Properties of Rasagiline, N-Propargylamine-1(R)-aminoindan, and Its Optical (S)-Isomer, TV1022" Ann NY Acad Sci., 939:320-329 (2001).

W. Maruyama et al.,"Neurotoxins induce apoptosis in dopamine neurons: protection by N-propargylamine-1(R)-and (S)-aminoindan, rasagiline and TV1022", Journal Neural Transm Suppl., 60:171-186 (2002).

M. Youdim et al.,"The essentiality of Bcl-2, PKC and proteasome-ubiquitin complex activations in the neuroprotective-antipoptopic action of the anti-Parkinson drug, rasagiline", Biochemical Pharmacology 66 1635-1641(2003).

W. Maruyama et al., "Anti-apoptic action of anti-Alzheimer drug, TV3326 [(N-propargyl)-(3R)-aminoindan-5-yl]-ethyl methyl carbamate, a novel cholinesterase-monoamine oxidase inhibitor" Neuroscience Letters 341 233-236 (2003).

V. Pursiainen, "Selegiline and blood pressure in patients with Parkinson's disease", Acta. Neurol. Scand. 115:104-108 (2007).

Richardson et al., "Report of the 1995 World Health Organization/ International Society and Federation of Cardiology Task Force on the Definition and Classification of Cardiomyopathies", American Heart Association Circulation 93:841-842 (1996).

Rodriguez et al., Apoptosis in myocardial infarction Annals of Medicine, 2002, 34, 470-479 (1996).

N. Serbecic et al., "Anti-oxidative vitamins prevent lipid-peroxidation and apoptosis in corneal endothelial cells", Cell Tissue Res 320:465-475 (2005).

CB Seymore et al., "Monoamine oxidase inhibitors/-deprenyl and clorgyline protect nonmalignant human cells from ionising radiation and chemotherapy toxicity", British Journal of Cancer 89: 1979-1986 (2003).

L. L. Simpson, "Evidence that deprenyl, a type B monoamine oxidase inhibitor, is an indirectly acting sympathomimetic amine" Abstract (1977).

Stephanou et al., "Induction of Apoptosis and Fas Receptor/Fas Ligand Expression by Ischemia/Reperfusion in Cardiac Myocytes Requires Serine 727 of the STAT-1 Transcription Factor but Not Tyrosine 701." The Journal of Biological Chemistry 276(30); 28340-28347 (2001).

W.G. Tatton et al., "(-)-Deprenyl reduces neuronal apoptosis and facilitates neuronal outgrowth by altering protein synthesis without inhibiting monoamine oxidase", J. Neural Transm [Suppl] 48: 45-59. (1996).

Weinreb et al, "Neuroprotection via pro-survival protein kinase C isoforms associated with Bcl-2 family members", The FASEB Journal express, article 10.1096/fj.04-1916fje. Published online Jul. 9, 2004.

WHO Taskforce., "Report of the WHO/ISFC task force on the definition and classification of cardiomyopathies", Br Heart J. 44:672-3 (1980).

M. Youdim et al.,"The Anti-Parkinson Drug Rasagiline and Its Cholinesterase Inhibitor Derivatives Exert Neuroprotection Unrelated to MAO Inhibition in Cell Culture and in Vivo", Ann NY Acad Sci., 939, 450-458 (2001).

H. Yi et al., "N-Propargylamine protects SH-SY5Y cells from apoptosis induced by an endogenous neurotoxin, N-methyl(R)salsolinol, through stabilization of mitochondrial membrane and induction of anti-apoptic Bcl-2", J. Neural Transm 113: 21-32 (2006).

M. Yogev-Falach et al.,"The importance of propargylamine moiety in the anti-Parkinson drug rasagiline and its derivatives in MAPK-dependent amyloid precursor protein processing", FASEB Journal 2325-2327 (2003).

M. Youdim et al.,"Rasagiline [N-propargyl-1R(+)-aminoindan], a selective and potent inhibitor of mitochondrial monoamine oxidase B", British Journal of Pharmacology 132, 500-506 (2001).

M. Youdim et al., "Therapeutic Applications of Selective and Non-Selective Inhibitors of Monoamine Oxidase A and B that do not Cause Significant Tryamine Potentiation", NeuroToxicology 25:243-250 (2004).

Youdim, MBH "Novel bifunctional drugs targeting monoamine oxidase inhibition and iron chelation as an approach to neuroprotection in Parkinson's disease and other neurodegenerative diseases," J. Neural Transm. (2004) 111:1455-1471.

Qin et al.,"Selegiline attenuates cardiac oxidative stress and apoptosis in heart failure: association with improvement of cardiac function" European Journal of Pharmacology 461, pp. 149-158 (2003).

Naoi et al.,"Anti-apoptotic function of propargylamine inhibitors of type-B monoamine oxidase" Inflammopharmacology 11, pp. 175-181 (2003).

* cited by examiner

Control    Apoptosis

METHODS FOR TREATMENT OF CARDIOVASCULAR DISORDERS AND DISEASES

CROSS-REFERENCE TO RELATED APPLICATIONS

The present application is a continuation-in-part application of U.S. patent application Ser. No. 10/952,367, filed Sep. 29, 2004, now abandoned and claims the benefit of U.S. Provisional Patent Application No. 60/524,616, filed Nov. 25, 2003, now expired, and U.S. Provisional Patent Application No. 60/570,496, filed May 13, 2004, now expired, the entire contents of each and all these applications being herewith incorporated by reference in their entirety as if fully disclosed herein.

FIELD AND BACKGROUND OF THE INVENTION

The present invention relates to compositions and methods for the treatment of cardiovascular disorders and diseases and, more particularly, to propargylamine and derivatives thereof for use in said compositions and methods.
Cardiovascular Disorders and Diseases Cardiovascular disorders and diseases and their associated complications are a principal cause of disabilities and deaths of individuals in the United States and Western Europe. For example, in recent years more than 500,000 deaths have occurred annually in the United States alone as a result of coronary artery disease, and an additional 700,000 patients have been hospitalized for myocardial infarction.

Ischemic heart disease (IHD) is the most common, serious, chronic, life-threatening illness among the cardiovascular disorders and diseases. Ischemia, reduced myocardial perfusion, which causes lack of oxygen (hypoxia) as well as other metabolic changes, is the most common effect resulting from an inadequate blood flow through the coronary arteries, which are the blood suppliers of the heart. The most common cause of myocardial ischemia is the atherosclerotic disease of epicardial coronary arteries. The plaques consist of subintimal collections of fat, cells, and debris, which develop at irregular rates in different segments of the epicardial coronary tree, and lead eventually to segmental reductions in cross-sectional area (stenosis). When the coronary artery cross-section area is reduced by ~75%, a full range of increases in flow to meet increased myocardial demand is not possible. When the luminal area is reduced by more than 80%, blood flow at rest may be reduced, and further minor decreases in the stenotic orifice can reduce coronary flow dramatically and cause myocardial ischemia and infarction. This situation impairs myocardial contractility during exercise, creating the chest angina. Critical stenosis of the coronaries can cause chest angina even at rest, implying that the myocardium is suffering from lack of perfusion. The most serious complication of ischemic heart disease is acute myocardial infarction (AMI), which is one of the most common diagnoses in hospitalized patients. AMI generally occurs when coronary blood flow decreases abruptly after a thrombotic occlusion of a coronary artery, previously narrowed by atherosclerotic plaque. Although the mortality rate after admission for AMI has declined by about 30% over the last two decades, approximately 1 of every 25 patients who survives the initial hospitalization dies in the first year after AMI. The first step is the dissection of the atherosclerotic plaque, which causes the exposure of the thrombogenic plaque core to the blood. Because of its high thrombogenicity, a thrombus consists mainly of fibrin and activated thrombocyte is rapidly growing from the plaque core. Consequently, blood flow is seriously disturbed until there is no sufficient blood flow to the myocardium and an infarction begins due to lack of perfusion of oxygen.

There are various insults which cause the myocardial damage during myocardial ischemia and infarction. Lack of adequate perfusion to the heart tissue may result in: (i) lack of oxygen (hypoxia); (ii) growth factors and nutrients deprivation (e.g., IGF-1, insulin, glucose); (iii) acidosis (lactic acid production); (iv) hyperkalemia (due to environmental acidosis and cell damage); and/or (v) during ischemia, but mostly following reperfusion (resumption of the blood flow to the ischemic tissue), reactive oxygen species (ROS) such as $H_2O_2$, $O_2^-$ $OH^-$ are created by the ischemic cells and by damage to neighboring cells. Each and every of these insults has been shown to exert damage to cardiomyocytes both in vivo and in vitro.

Two main cellular death types occur in nature: necrosis and apoptosis. While necrosis is a random process, often initiated by hostile environmental stimuli, apoptosis is a programmed cell death in which distinct intracellular signaling pathways are activated. Apoptosis is a fundamental physiological and pathologic mechanism that allows elimination of no-longer useful cells during embryogenesis, or of aged or damaged cells during life. Unlike necrosis, which involves large number of cells, apoptosis usually affects small number of cells without inflammation. In apoptosis, the nuclear DNA is "digested" into small fragments by special DNAses, while cytoskeletal and myofibrillar proteins are degraded by specialized proteases as well. At the final stages, the cell dissolves into a characteristic membrane bound vesicles (apoptotic bodies), which are quickly phagocyted by phagocytic neighboring cells.

Cells can undergo apoptosis caused by intrinsic stimuli, e.g. hypoxia, ROS, chemotherapies, or by extrinsic stimuli, mainly referred to activation of death receptors such as TNF-α and Fas.

Fas is a ubiquitous cell-surface receptor involved in apoptosis initiation. Fas belongs to the TNF/NGF superfamily, and is activated by Fas Ligand (FasL), which may cause apoptosis in Fas-bearing cells (Berke, 1997). It appears that while healthy cardiomyocytes are resistant to Fas-mediated apoptosis, during cardiac pathologies cardiomyocytes become sensitive to Fas-mediated apoptosis. Recent studies suggest that in several important heart diseases such as myocarditis, hypertrophy, ischemia, ischemia/reperfusion and heart failure, Fas activation results in apoptotic as well as in non-apoptotic effects, both contributing to cardiac dysfunction (Haunstetter and Izumo, 1998; Binah, 2000). Recent studies have shown that Fas activation is involved not only in myocardial pathologies inflicted by immune effectors (CTLs) such as transplant rejection, myocarditis and the resulting dilated cardiomyopathy (Binah, 2000; Hershkowitz et al., 1987), but also in lymphocyte-independent diseases such as ischemia/reperfusion injuries (Fliss and Gattinger, 1996; Yaoita et al., 1998; Jeremias et al., 2000). In this regard, it was recently proposed that FasL can be cleaved by a metalloprotease to form soluble FasL (sFasL), which can cause apoptosis in susceptible cells. Therefore, sFasL, which may be secreted from the failing heart and is elevated in patients with advanced congestive heart failure (Yamaguchi et al., 1999), is a potential contributor to apoptosis in this wide-spread heart pathology.

Programmed cell death (apoptosis) is recognized, increasingly, as a contributing cause of cardiac myocyte loss with ischemia/reperfusion injury, myocardial infarction, and long-standing heart failure.

Propargylamine and Propargylamine Derivatives

Several propargylamine derivatives have been shown to selectively inhibit monoamine oxidase (MAO)-B and/or MAO-A activity and, thus to be suitable for treatment of neurodegenerative diseases such as Parkinson's and Alzheimer's disease. In addition, these compounds have been further shown to protect against neurodegeneration by preventing apoptosis.

Rasagiline, R(+)—N-propargyl-1-aminoindan, a highly potent selective irreversible monoamine oxidase (MAO)-B inhibitor, has been shown to exhibit neuroprotective activity and antiapoptotic effects against a variety of insults in cell cultures and in vivo.

Rasagiline has been developed for Parkinson's disease as monotherapy or as an adjunct to L-dopa therapy (Youdim et al., 2001; Parkinson Study Group, 2002; Finberg and Youdim, 2002; Gassen et al., 2003). Phase III controlled studies have shown that rasagiline is effective with a dose of as low as 1 mg/kg in monotherapy (Parkinson Study group, 2002) and as an adjunct to L-dopa, comparable in its effect to the anti-Parkinson catechol-O-methyltranferase (COMT) inhibitor, entacapone (Brooks and Sagar, 2003). Rasagiline has recently finished the phase III clinical trials and has been approved for treatment of Parkinson's disease in Europe, Israel, and in the U.S.

Rasagiline exhibits neuroprotective activities both in vitro and in vivo (for review see Mandel et al., 2003; Youdim, 2003) which may contribute to its possible disease modifying activity. It is metabolized to its major two metabolites: aminoindan (here designated "TVP-136") and S(−)—N-propargyl-1-aminoindan (here designated "TVP-1022") (Youdim et al., 2001), which also have neuroprotective activity against serum deprivation and 1-methamphetamine-induced neurotoxicity in partially differentiated PC-12 cells (Am et al., 2004).

Rasagiline [R(+)—N-propargyl-1-aminoindan] and pharmaceutically acceptable salts thereof were first disclosed in US patents U.S. Pat. Nos. 5,387,612, 5,453,446, 5,457,133, 5,576,353, 5,668,181, 5,786,390, 5,891,923, and U.S. Pat. No. 6,630,514 as useful for the treatment of Parkinson's disease, memory disorders, dementia of the Alzheimer type, depression, and the hyperactive syndrome. The 4-fluoro-, 5-fluoro- and 6-fluoro-N-propargyl-1-aminoindan derivatives were disclosed in U.S. Pat. No. 5,486,541 for the same purposes.

U.S. Pat. Nos. 5,519,061, 5,599,991, 5,744,500, 6,277,886, 6,316,504, 5,576,353, 5,668,181, 5,786,390, 5,891,923, and U.S. Pat. No. 6,630,514 disclose R(+)—N-propargyl-1-aminoindan and pharmaceutically acceptable salts thereof as useful for treatment of additional indications, namely, an affective illness, a neurological hypoxia or anoxia, neurodegenerative diseases, a neurotoxic injury, stroke, brain ischemia, a head trauma injury, a spinal trauma injury, schizophrenia, an attention deficit disorder, multiple sclerosis, and withdrawal symptoms.

U.S. Pat. No. 6,251,938 describes N-propargyl-phenylethylamine compounds, and U.S. Pat. Nos. 6,303,650, 6,462,222 and U.S. Pat. No. 6,538,025 describe N-propargyl-1-aminoindan and N-propargyl-1-aminotetralin compounds, said to be useful for treatment of depression, attention deficit disorder, attention deficit and hyperactivity disorder, Tourette's syndrome, Alzheimer's disease and other dementia such as senile dementia, dementia of the Parkinson's type, vascular dementia and Lewy body dementia.

The first compound found to selectively inhibit MAO-B was R—(−)—N-methyl-N-(prop-2-ynyl)-2-aminophenyl-propane, also known as L-(−)-deprenyl, R—(−)-deprenyl, or selegiline. In addition to Parkinson's disease, other diseases and conditions for which selegiline is disclosed as being useful include: drug withdrawal (WO 92/21333, including withdrawal from psychostimulants, opiates, narcotics, and barbiturates); depression (U.S. Pat. No. 4,861,800); Alzheimer's disease and Parkinson's disease, particularly through the use of transdermal dosage forms, including ointments, creams and patches; macular degeneration (U.S. Pat. No. 5,242,950); age-dependent degeneracies, including renal function and cognitive function as evidenced by spatial learning ability (U.S. Pat. No. 5,151,449); pituitary-dependent Cushing's disease in humans and nonhumans (U.S. Pat. No. 5,192,808); immune system dysfunction in both humans (U.S. Pat. No. 5,387,615) and animals (U.S. Pat. No. 5,276,057); age-dependent weight loss in mammals (U.S. Pat. No. 5,225,446); schizophrenia (U.S. Pat. No. 5,151,419); and various neoplastic conditions including cancers, such as mammary and pituitary cancers. WO 92/17169 discloses the use of selegiline in the treatment of neuromuscular and neurodegenerative disease and in the treatment of CNS injury due to hypoxia, hypoglycemia, ischemic stroke or trauma. In addition, the biochemical effects of selegiline on neuronal cells have been extensively studied (e.g., see Tatton, et al., 1991 and 1993). U.S. Pat. No. 6,562,365 discloses the use of desmethylselegiline for selegiline-responsive diseases and conditions.

Selegiline (1-deprenyl) is a selective MAO-B inhibitor which is a useful anti-Parkinson drug both in monotherapy (Parkinson Study Group, 1989) and as an adjunct to L-DOPA therapy, and has L-DOPA sparing action (Birkmayer et al., 1977; Riederer and Rinne, 1992; Parkinson Study Group, 1989). Selegiline is a propargyl derivative of 1-methamphetamine and thus its major metabolite is 1-methamphetamine (Szoko et al., 1999; Kraemer and Maurer, 2002; Shin, 1997), which is neurotoxic (Abu-Raya et al., 2002; Am et al., 2004). In contrast to aminoindan, a rasagiline metabolite, L-methamphetamine prevents the neuroprotective activities of rasagiline and selegiline in partially differentiated cultured PC-12 cells (Am et al., 2004).

Selegiline and methamphetamine, unlike rasagiline and aminoindan, have sympathomimetic activity (Simpson, 1978) that increases heart rate and blood pressure (Finberg et al., 1990; Finberg et al., 1999). Recent studies (Glezer and Finberg, 2003) have indicated that the sympathomimetic action of selegiline can be attributed to its 1-methamphetamine and amphetamine metabolites. These properties are absent in rasagiline and in its metabolite aminoindan. Parkinsonian patients receiving combined treatments with selegiline plus levodopa have been reported to have a higher mortality rate than those treated with levodopa alone (Lees, 1995). This is not related to the MAO-B inhibitory activity of selegiline, but is rather attributed to its sympathomimetic action and methamphetamine metabolites (Reynolds et al., 1978; Lavian et al., 1993).

Several propargylamine derivatives have been shown to selectively inhibit MAO-B and/or MAO-A activity and, thus to be suitable for treatment of neurodegenerative diseases such as Parkinson's and Alzheimer's disease. In addition, these compounds have been further shown to protect against neurodegeneration by preventing apoptosis.

U.S. Pat. Nos. 5,169,868, 5,840,979 and U.S. Pat. No. 6,251,950 disclose aliphatic propargylamines as selective MAO-B inhibitors, neuroprotective and cellular rescue agents. The lead compound, (R)-N-(2-heptyl)methyl-propargylamine(R-2HMP), has been shown to be a potent MAO-B inhibitor and antiapoptotic agent (Durden et al., 2000).

Propargylamine was reported many years ago to be a mechanism-based inhibitor of the copper-containing bovine plasma amine oxidase (BPAO), though the potency was modest. U.S. Pat. No. 6,395,780 discloses propargylamine as a weak glycine-cleavage system inhibitor. Copending U.S. patent application Ser. No. 10/952,379, entitled "Use of propargylamine as neuroprotective agent", filed on Sep. 29, 2004, discloses that propargylamine exhibits neuroprotective and anti-apoptotic activities and can, therefore, be used for all known uses of rasagiline and similar drugs containing the propargylamine moiety.

Copending U.S. patent application Ser. No. 11/244,150, entitled "Methods for treatment of renal failure", filed on Oct. 6, 2005, discloses a method for treatment of a renal failure, either acute or chronic, which comprises administering to the subject an amount of an active agent selected from the group consisting of propargylamine, a propargylamine derivative, and a pharmaceutically acceptable salt thereof.

All and each of the above-mentioned US patents and patent applications are herewith incorporated by reference in their entirety as if fully disclosed herein.

SUMMARY OF THE INVENTION

The present invention relates to a method for treatment of a subject susceptible to or suffering from a cardiovascular disorder, disease or condition which comprises administering to the subject an amount of an agent selected from the group consisting of propargylamine, a propargylamine derivative and a pharmaceutically acceptable salt thereof, effective to treat the subject.

In one preferred embodiment of the invention, the agent is propargylamine or a pharmaceutically acceptable salt thereof. In another preferred embodiment, the agent is a propargylamine derivative such as an N-propargyl-1-aminoindan, e.g. R(+)—N-propargyl-1-aminoindan (rasagiline) or its enantiomer S(−)—N-propargyl-1-aminoindan (TVP1022), and analog thereof, or a pharmaceutically acceptable salt thereof.

The methods and compositions of the invention are suitable for preventing and/or treating congestive heart failure (CHF), cardiac hypertrophy including both atrial and ventricular hypertrophy, myocardial infarction, myocardial ischemia, myocardial ischemia and reperfusion, cardiomyopathies, or arrhythmias.

BRIEF DESCRIPTION OF THE FIGURES

FIG. 1A-*control*.

DETAILED DESCRIPTION OF THE INVENTION

Figure 1A:
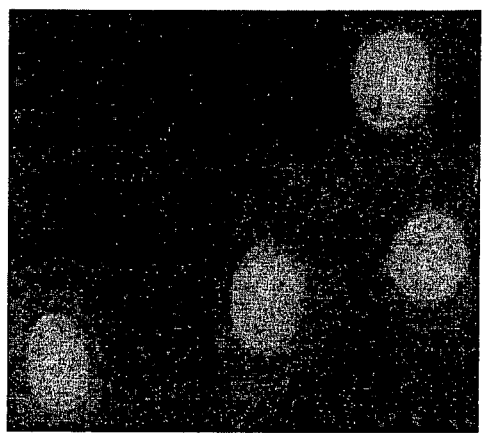
FIGS. 1A-1B depict apoptosis induced in H9c2 rat heart cells by means of recombinant Fas ligand (rFasL). The apoptotic cells detected by DAPI staining are marked by the arrows (FIG. 1B).

As described in detail in the Examples section hereinafter, propargylamine and propargylamine derivatives such as rasagiline and its enantiomer S(−)—N-propargyl-1-aminoindan (also designated TVP 1022) provide protection against apoptosis induced by several means in the embryonic cardiac cell line H9c2 or in neonatal rat ventricular myocytes (NRVM), as well as against hypertrophy induced by Fas receptor activation.

In particular, it has been found in accordance with the present invention that propargylamine and TVP1022, which do not inhibit monoamine oxidase, decrease the expression of key pro-apoptotic proteins such as caspase-3 and cytosolic cytochrome C, and increase the expression of anti-apoptotic proteins such as mitochondrial Bcl-2 and PKC-ε, thus shifting the balance between the anti- and the pro-apoptotic proteins towards the former and generating anti-apoptotic effect. These studies have been conducted both in in vitro and in vivo experiments, in which both naïve and volume overload-induced congestive heart failure (CHF) rats have been used. Furthermore, as clearly demonstrated in Example 10, pretreatment with propargylamine or TVP 1022 blocks the volume overload induced hypertrophy in CHF rats and the reduction in ventricular mechanical function as derived from echocardiological parameters.

The present invention thus relates to a method for treatment of a subject susceptible to or suffering from a cardiovascular disorder, disease or condition which comprises administering to the subject an amount of an agent selected from the group consisting of propargylamine, a propargylamine derivative, or a pharmaceutically acceptable salt thereof, effective to treat the subject.

The present invention further relates to a method for treatment of a subject susceptible to or suffering from a cardiovascular disorder, disease or condition which comprises administering to the subject an amount of an agent selected from the group consisting of propargylamine, a propargylamine derivative, or a pharmaceutically acceptable salt thereof, effective to protect ventricular muscle from apoptosis, particularly Fas-mediated apoptosis, wherein said cardiovascular disorder or disease is ischemia/reperfusion injury, myocardial infarction, and long-standing heart failure.

In one preferred embodiment, the active agent used in the present invention is propargylamine or a pharmaceutically acceptable salt thereof. The use of any physiologically acceptable salt of propargylamine is encompassed by the present invention such as the hydrochloride, hydrobromide, sulfate, mesylate, esylate, tosylate, sulfonate, phosphate, or carboxylate salt. In more preferred embodiments, propargylamine hydrochloride and propargylamine mesylate are used according to the invention.

In another preferred embodiment, the active agent used in the present invention is N-propargyl-1-aminoindan, either in its racemic form (described, for example, in U.S. Pat. No. 6,630,514) or as the R-enantiomer R(+)—N-propargyl-1-aminoindan (rasagiline, described, for example, in U.S. Pat. No. 5,387,612) or as the S-enantiomer S—(−)—N-propargyl-1-aminoindan (TVP1022, described, for example, in U.S. Pat. No. 6,277,886). In a more preferred embodiment of the invention, the active agent is rasagiline, the R(+)—N-propargyl-1-aminoindan, or its enantiomer S(−)—N-propargyl-1-aminoindan.

In another preferred embodiment, the active agent is a pharmaceutically acceptable salt of N-propargyl-1-aminoindan or of an enantiomer thereof including, but not limited to, the mesylate, maleate, fumarate, tartrate, hydrochloride, hydrobromide, esylate, p-toluenesulfonate, benzoate, acetate, phosphate and sulfate salts. In preferred embodiments, the salt is a pharmaceutically acceptable salt of R(+)—N-propargyl-1-aminoindan such as, but not limited to, the mesylate salt (described, for example, in U.S. Pat. No. 5,532,415), the esylate and the sulfate salts (both described, for example, in U.S. Pat. No. 5,599,991), and the hydrochloride salt (described, for example, in U.S. Pat. No. 6,630,514) of R(+)—N-propargyl-1-aminoindan or S(−)—N-propargyl-1-aminoindan.

In a further embodiment, the active agent is an analog of N-propargyl-1-aminoindan, an enantiomer or a pharmaceutically acceptable salt thereof. In one embodiment, the analogs are the compounds described in U.S. Pat. No. 5,486,541 such as, but not limited to, the compounds 4-fluoro-N-propargyl-1-aminoindan, 5-fluoro-N-propargyl-1-aminoindan, 6-fluoro-N-propargyl-1-aminoindan, an enantiomer thereof and pharmaceutically acceptable addition salts thereof. In another embodiment, the analogs are the compounds described in U.S. Pat. No. 6,251,938 such as, but not limited to, the compounds (rac)-3-(N-methyl,N-propyl-carbamyloxy)-α-methyl-N'-propargyl phenethylamine HCl; (rac)-3-(N,N-dimethyl-carbamyloxy)-α-methyl-N'-methyl, N'-propargyl phenethylamine HCl; (rac)-3-(N-methyl,N-hexyl-carbamyloxy)-α-methyl-N'-methyl, N'-propargyl phenethylamine mesylate; (rac)-3-(N-methyl,N-cyclohexyl-carbamyloxy)-α-methyl-N'-methyl,N'-propargylphenethyl HCl; and (S)-3-(N-methyl, N-hexyl-carbamyloxy)-α-methyl-N'-methyl,N'-propargyl phenethylamine ethane-sulfonate. In a further embodiment, the analogs are the compounds described in U.S. Pat. No. 6,303,650 such as, but not limited to, the compounds (rac) 6-(N-methyl, N-ethyl-carbamyloxy)-N'-propargyl-1-aminoindan HCl; (rac) 6-(N,N-dimethyl, carbamyloxy)-N'-methyl-N'-propargyl-1-aminoindan HCl; (rac) 6-(N-methyl, N-ethyl-carbamyloxy-N'-propargyl-1-aminotetralin HCl; (rac) 6-(N,N-dimethyl-thiocarbamyloxy)-1-aminoindan HCl; (rac) 6-(N-propyl-carbamyloxy-N'-propargyl-1-aminoindan HCl; (rac) 5-chloro-6-(N-methyl, N-propyl-carbamyloxy)-N'-propargyl-1-aminoindan HCl; (S)-6-(N-methyl), N-propyl-carbamyloxy)-N'-propargyl-1-aminoindan HCl; and (R)-6-(N- methyl, N-ethyl-carbamyloxy)-N'-propargyl-1-aminoindan hemi-(L)-tartrate, and 6-(N-methyl, N-ethyl-carbamyloxy)-N'-methyl,N'-propargyl-1-aminoindan described in U.S. Pat. No. 6,462,222.

In a still further embodiment, the active agent is an aliphatic propargylamine described in U.S. Pat. Nos. 5,169,868, 5,840,979 and U.S. Pat. No. 6,251,950 such as, but not limited to, the compounds N-(1-heptyl)propargylamine; N-(1-octyl) propargylamine; N-(1-nonyl)propargylamine; N-(1-decyl) propargylamine; N-(1-undecyl)propargylamine: N-(1-dodecyl)propargylamine; R—N-(2-butyl)propargylamine; R—N-(2-pentyl) propargylamine; R—N-(2-hexyl)propargylamine; R—N-(2-heptyl)propargylamine; R—N-(2-octyl)propargylamine; R—N-(2-nonyl)propargylamine; R—N-(2-decyl) propargylamine, R—N-(2-undecyl)propargylamine; R—N-(2-dodecyl)propargylamine: N-(1-butyl)-N-methylpropargylamine; N-(2-butyl)-N-methylpropargylamine; N-(2-pentyl)-N-methylpropargylamine; N-(1-pentyl)-N-methylpropargylamine; N-(2-hexyl)-N-methylpropargylamine; N-(2-heptyl)-N-methylpropargylamine; N-(2-decyl)-N-methylpropargylamine; N-(2-dodecyl)-N-methylpropargylamine; R(−)—N-(2-butyl)-N-methylpropargylamine; or a pharmaceutically acceptable salt thereof.

In yet another embodiment, the active agent is selegiline, desmethylselegiline or norprenyl, pargyline or chlorgyline.

In still another embodiment, the active agent is the compound N-methyl-N-propargyl-10-aminomethyl-dibenzo[b,f] oxepin (known as CGP 3466, described in Zimmermann et al., 1999).

All the US patents and other publications mentioned hereinabove are hereby incorporated by reference in their entirety as if fully disclosed herein.

In another aspect, the present invention provides a pharmaceutical composition for prevention and/or treatment of a cardiovascular disorder, disease or condition comprising a pharmaceutically acceptable carrier and an agent selected from the group consisting of propargylamine, a propargylamine derivative, or a pharmaceutically acceptable salt thereof as described above.

The pharmaceutical composition provided by the present invention may be in solid, semisolid or liquid form and may further include pharmaceutically acceptable fillers, carriers or diluents, and other inert ingredients and excipients. The composition can be administered by any suitable route, e.g. intravenously, orally, parenterally, rectally, or transdermally. The dosage will depend on the state of the patient and severity of the disease and will be determined as deemed appropriate by the practitioner.

In one embodiment, the pharmaceutically acceptable carrier is a solid and the pharmaceutical composition is in a suitable form for oral administration including tablets, compressed or coated pills, dragees, sachets, hard or soft gelatin capsules, and sublingual tablets. In a more preferred embodiment, the pharmaceutical composition is a tablet containing an amount of the active agent in the range of about 0.1-100 mg, preferably from about 1 mg to about 10 mg.

In another embodiment, the pharmaceutically acceptable carrier is a liquid and the pharmaceutical composition is an injectable solution. The amount of the active agent in the injectable solution is in the range of from about 0.1 mg/kg to about 100 mg/kg, more preferably 1 mg/kg to about 10 mg/kg.

For parenteral administration the invention provides ampoules or vials that include an aqueous or non-aqueous solution or emulsion. For rectal administration there are provided suppositories with hydrophilic or hydrophobic (gel) vehicles.

The methods and compositions of the invention are for preventing and/or treating congestive heart failure, cardiac hypertrophy including both atrial and ventricular hypertrophy, myocardial infarction, myocardial ischemia, myocardial ischemia and reperfusion, arrhythmias, or long-standing heart failure. In preferred embodiments, the cardiovascular disorder is congestive heart failure, and/or cardiac hypertrophy, and/or ischemia and/or arrhythmias.

The dosage and frequency of administration of the drug will depend from the age and condition of the patient, type of disorder and its severity, and will be determined according to the physician's judgment. It can be presumed that for preventive treatment of subjects susceptible to a cardiovascular disorder or disease lower doses will be needed while higher doses will be administered in acute cases. The susceptibility to cardiovascular disorder or disease may derive from diseases or disorders such as diabetes and obesity, or from genetic or ethnic factors. It has been reported that people with ancestry in South Asia are highly susceptible to cardiovascular diseases (BMJ, 2002, 324: 625-626).

In one embodiment of the invention, the active agent is administered alone. In other embodiments of the invention, the active agent is administered in combination with another known cardiovascular drug, either before, simultaneously or after said other cardiovascular drug.

The following examples illustrate certain features of the present invention but are not intended to limit the scope of the present invention.

EXAMPLES

Materials and Methods (i) Materials. Rasagiline, its enentiomer S(−)—N-propargyl-1-aminoindan (also designated here TVP1022), and propargylamine were kindly donated by Teva Pharmaceutical Industries Ltd. (Petach Tikva, Israel).

(ii) Cell Line H9c2. Experiments were performed on the embryonic rat heart cell line H9c2. H9c2 cells were cultured in DMEM (Biological Industries, Beit-Haemek, Israel) supplemented with 10% fetal calf serum (FCS), 50 units/ml penicillin G, 50 µg/ml streptomycin sulfate, 2 mg/ml L-glutamine and sodium pyruvate. H9c2 cells were harvested by trypsinization, washed with PBS, diluted to a concentration of $5 \times 10^4$ cells/ml with DMEM (high glucose) and cultured at 0.5 ml/well on sterile glass cover slips in 24-well plates.

(iii) Protocols Inducing Apoptosis (a) $H_2O_2$ Incubation protocol—To induce apoptosis, H9c2 cultures were exposed to $H_2O_2$ (0.5 µM) for 7 hours.

(b) Serum starvation—To induce apoptosis, H9c2 cultures were incubated in the culture medium containing 0% FCS for the indicated times.

(c) Activation of the Fas receptor—Fas activation was induced by incubating the cultures with recombinant human Fas Ligand (rFasL; 10 ng/ml) plus the enhancing antibody (1 µg/ml) for the indicated times, according to the manufacturer's recommendations (Alexis Biochemicals, San Diego, Calif.).

(iv) Determination of Apoptosis by DAPI. Cultures were counterstained with 4', 6-diamidino-2-phenylindole (DAPI) to visualize the nuclear morphology. Cells were scored as apoptotic, only if they exhibited unequivocal nuclear chromatin condensation and fragmentation.

(v) Animals. Studies were conducted on male Sprague Dawley rats (Harlan Laboratories Ltd., Jerusalem, Israel), weighing ~300 g. The animals were kept in a temperature-controlled room and maintained on standard rat diet (0.5% NaCl). All experiments were performed according to the guidelines of the Technion Committee for Supervision of Animal Experiments (Haifa, Israel). Heart failure was induced by surgical creation of an aortocaval fistula (AVF) between the abdominal aorta and the inferior vena cava (side to side, outer diameter 1-1.2 mm), which is a well established model of volume-overload induced heart failure, featuring many of the clinical symptoms of heart failure and dilated cardiomyopathy in humans. Sham-operated rats served as controls. Drugs (or saline as control) were orally administered, starting 7 days prior to surgery (day 0) and were continued for 21 days. Surgery was performed on day 7 and animals sacrificed 14 days post-surgery (day 21). Cardiac function was determined by echocardiography on days 0, 10 (3 days post-surgery) and 21 (before sacrifice). After the last echocardiography measurement, rats were sacrificed and hearts were analyzed.

Example 1

Rasagiline, S(−)—N-propargyl-1-aminoindan and Propargylamine Protect H9c2 Heart Cells Against Apoptosis Induced by Fas Activation The first apoptosis-inducing protocol tested was activation of the Fas receptor with recombinant Fas Ligand (rFasL) plus the enhancing antibody (Yaniv et al., 2002).

Figure 1B:
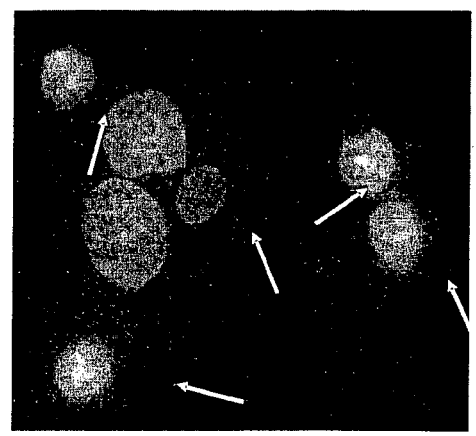

Cultures of embryonic rat heart cell line H9c2 were incubated with rFasL (10 ng/ml) and an enhancing antibody for periods of time of 9, 10 and 24 hours, and apoptosis measured thereafter. As shown in FIG. 1B, Fas activation caused prominent apoptosis in H9c2 cells, as detected by the DAPI assay.

Figure 2A:
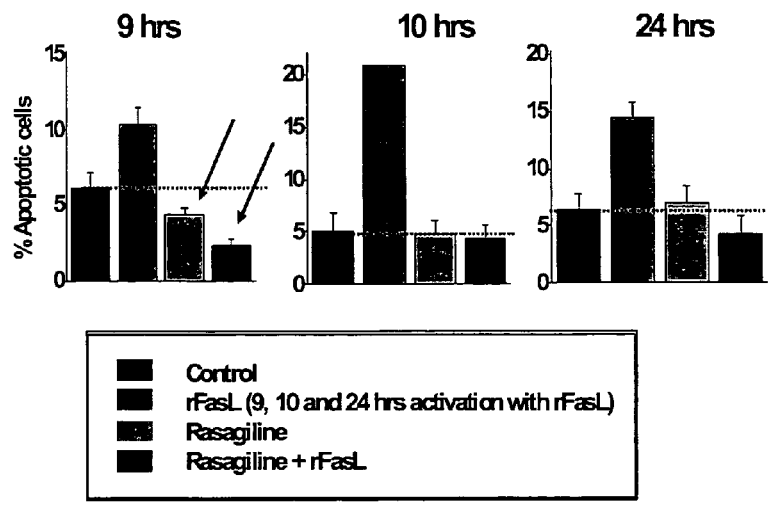
FIGS. 2A-2C show that rasagiline, S(−)—N-propargyl-1-aminoindan (TVP1022) and propargylamine block Fas-mediated apoptosis in H9c2 cells. Maximal apoptotic effect of Fas activation, attained at 10 hours incubation with rFasL, was completely prevented by 10 μM rasagiline (2A). Apoptotic effect of Fas activation, attained at ~10 hours incubation with rFasL, was completely prevented by both TVP1022 (0.1 or 1.0 μM) (2B) and propargylamine (0.1 or 1.0 μM) (2C).

In order to determine whether rasagiline can prevent Fas-mediated apoptosis, the Fas receptor was activated for 9, 10 and 24 hours as described above. Rasagiline (10 μM) was introduced to the culture medium 16 hours before, and was present throughout the apoptosis-inducing protocol (n=3 wells). As seen in FIG. 2A, the maximal apoptotic effect (~20% apoptosis) of Fas activation was attained at 10 hours incubation with rFasL. This apoptotic effect was completely prevented by rasagiline, demonstrating that rasagiline blocks Fas-mediated apoptosis.

Figure 2B:
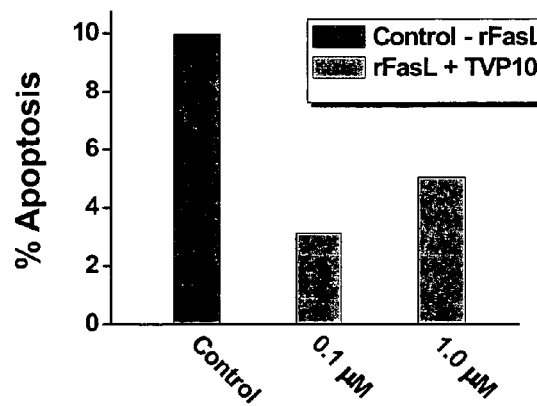
Figure 2C:
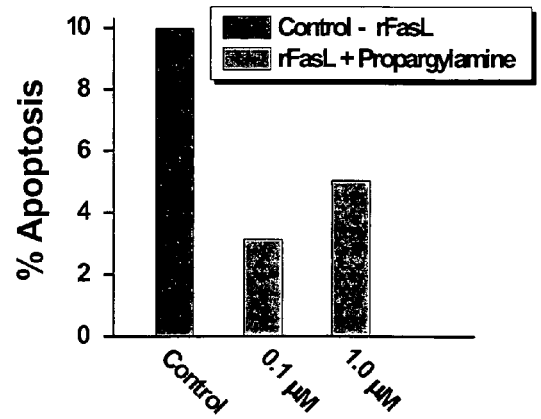

Similar results were obtained using the S-enantiomer, S(−)—N-propargyl-1-aminoindan, and propargylamine. Each one of the drugs, at a concentration of either 0.1 or 1.0 μM was introduced to the culture medium 16 hours before, and was presented throughout the apoptosis-inducing protocol (n=3 wells). As shown in FIGS. 2B-2C, the Fas-mediated apoptosis was ~10%, attained at ~10 hours incubation with rFasL, and it was completely prevented by both S(−)—N-propargyl-1-aminoindan (2B) and propargylamine (2C).

Example 2

Figure 3A:
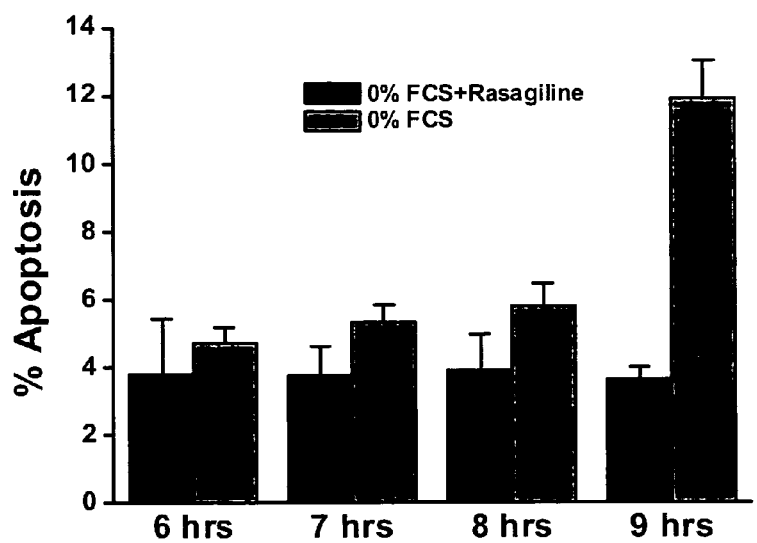
FIGS. 3A-3E show that rasagiline, propargylamine and S(−)—N-propargyl-1-aminoindan (TVP1022) protect against serum starvation-induced apoptosis in H9c2 cells: (3A) maximal apoptotic effect, induced by 9 hours serum starvation, was completely prevented by 10 μM rasagiline; (3B-3D) anti-apoptotic effects obtained by either 0.1-10 μM rasagiline, 0.01-1μM propargylamine or 0.01-1 μM TVP1022, respectively; (3E) anti-apoptotic effect obtained by 0.1-10 μM TVP 1022, using the MTT staining assay as a measure for apoptosis.

Rasagiline, S(−)—N-propargyl-1-aminoindan and Propargylamine Protect H9c2 Heart Cells Against Apoptosis Induced by Serum Starvation The next apoptosis-inducing stimulus tested was serum starvation (24 hrs, 0% serum in the culture medium). To induce apoptosis, H9c2 cells were incubated in the culture medium containing 0% FCS for 6, 7, 8 or 9 hours. Rasagiline (10 μM) was introduced to the culture medium 2 hours before inducing serum starvation and was present throughout the apoptosis-inducing protocol (n=3 wells). As seen in FIG. 3A, the most effective protocol was 9 hrs serum starvation, which caused 12% apoptosis. This effect was completely prevented by rasagiline.

Figure 3B:
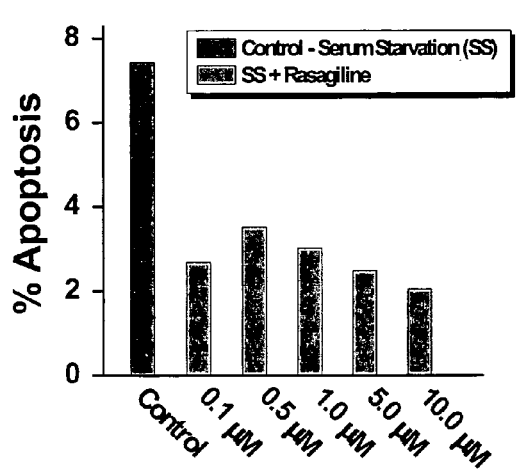
Figure 3C:
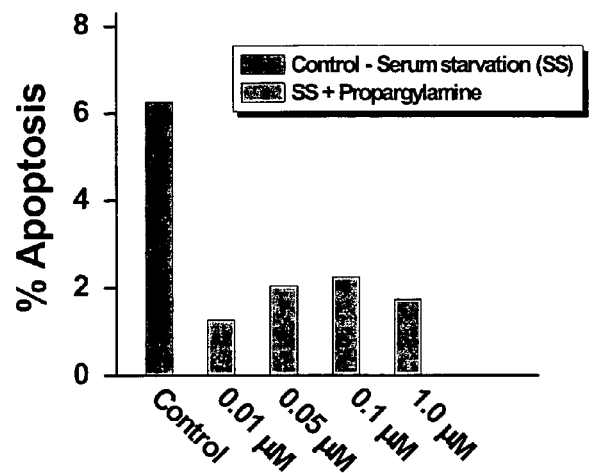
Figure 3D:
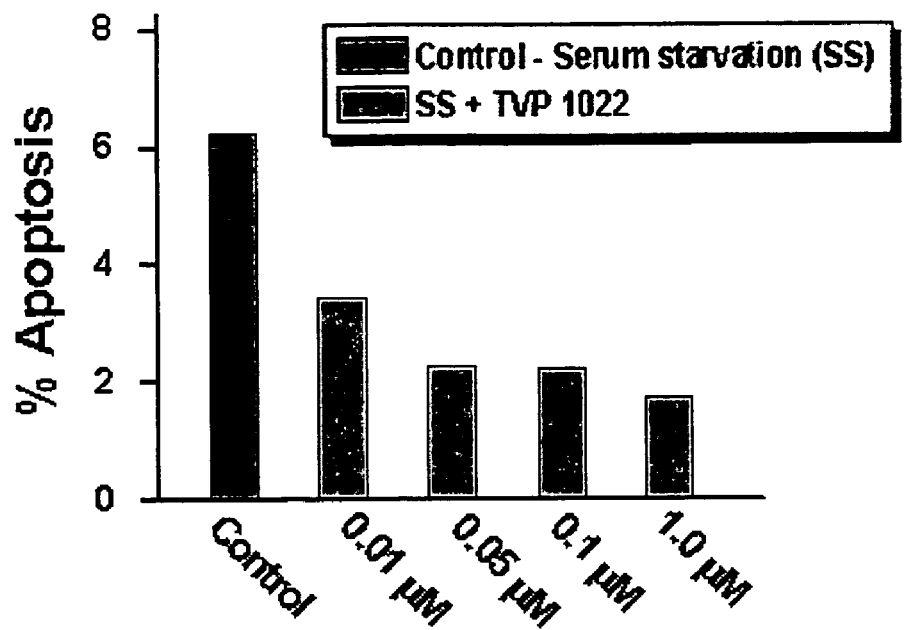
Figure 3E:
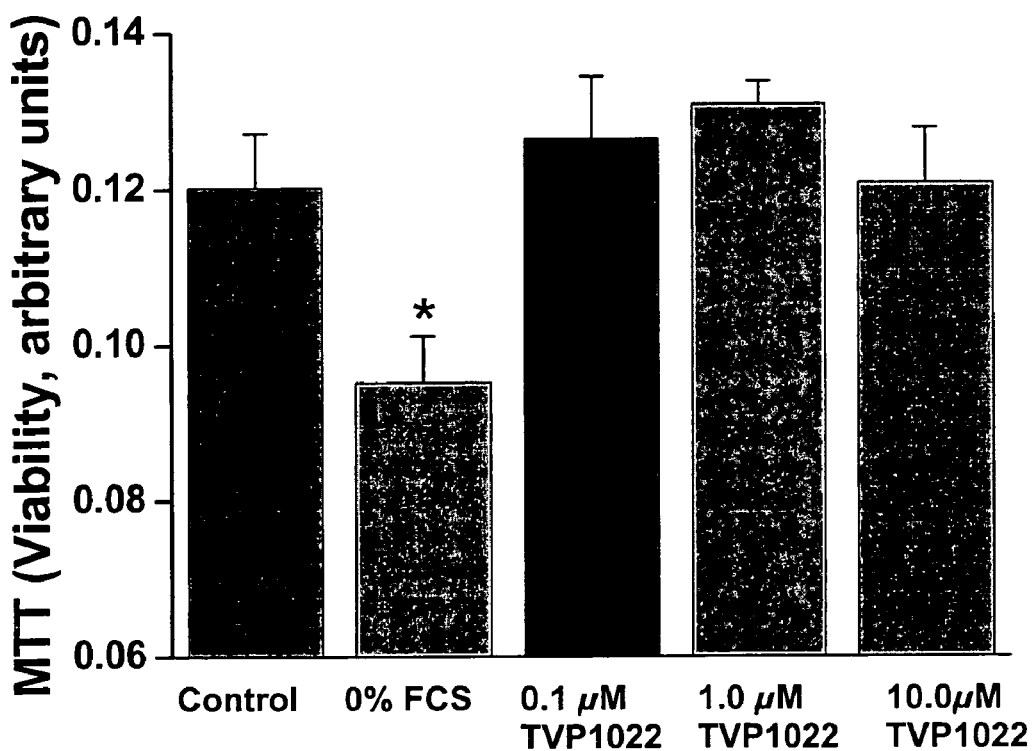

In the next stage, H9c2 cells were incubated in the culture medium containing 0% FCS for 24 hours, and the anti-apoptotic effect obtained by various concentrations of rasagiline, S(−)—N-propargyl-1-aminoindan and propargylamine was measured. FIG. 3B shows the anti-apoptotic effect obtained by rasagiline (0.1-10 μM) introduced to the culture medium 2 hours before serum starvation, FIGS. 3C-3D show that similar anti-apoptotic effects were obtained by either S(−)—N-propargyl-1-aminoindan or propargylamine(0.01-1 μM), respectively, and FIG. 3E shows the anti-apoptotic effect obtained by S(−)—N-propargyl-1-aminoindan (0.1-10 μM) using the MTT (3-(4,5-dimethylthiazol-2-yl)-2,5-diphenyltetrazolium bromide) staining assay as a measure for apoptosis.

Example 3

Figure 4:
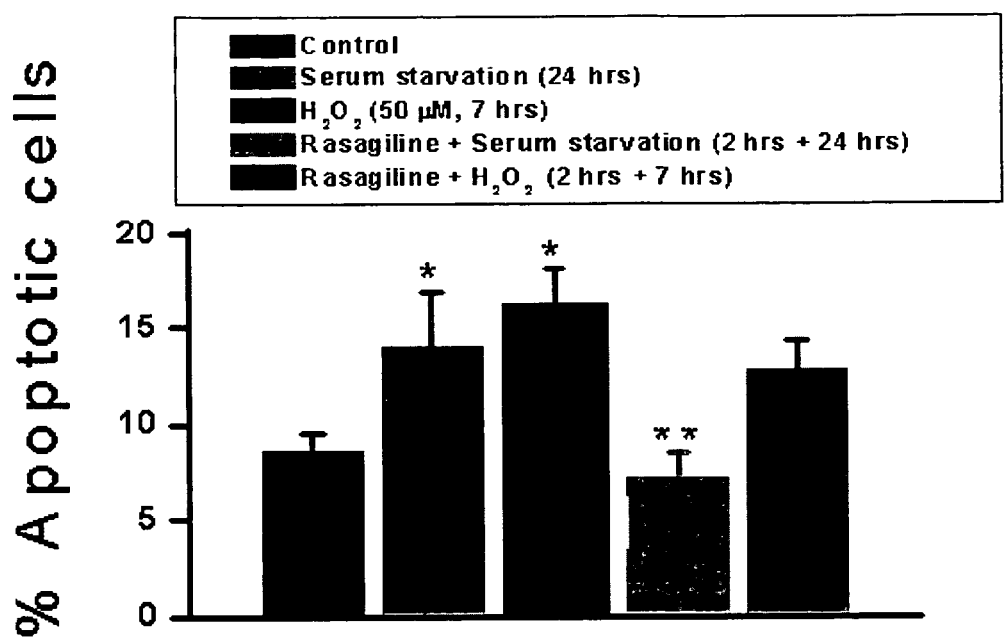
FIG. 4 shows that rasagiline protects against serum starvation-mediated but not $H_2O_2$— induced apoptosis in H9c2 cells (n=4 experiments, ~2000 cells counted). *compared to control. ** compared to serum starvation (p<0.05).

Rasagiline Protects H9c2 Heart Cells Against Apoptosis Induced by Serum Starvation but not $H_2O_2$-Induced Apoptosis In another experiment, we repeated the serum starvation protocol, and also tested in the same cultures whether rasagiline can protect against $H_2O_2$-induced apoptosis. Rasagiline was introduced to the culture medium 2 hours before inducing serum starvation or adding $H_2O_2$, and was present throughout the apoptosis-inducing protocol (n=4 experiments; ~2000 cells counted). As clearly shown in FIG. 4, rasagiline prevented the apoptosis induced by serum starvation (green bar), but not by $H_2O_2$ (gray bar).

Example 4

Rasagiline, S(−)—N-propargyl-1-aminoindan and Propargylamine Block Hypertrophy Induced by Activation of the Fas Receptor in Cultures of Neonatal Rat Ventricular Myocytes In neonatal rat ventricular myocytes (NRVM), activation of the Fas receptor does not cause apoptosis, but induces marked hypertrpohy.

In order to test whether rasagiline can prevent the marked hypertrophy induced in cultured neonatal rat ventricular myocytes (for methods, see Yaniv et al., 2002), Fas was activated for 24 hours by incubation with rFasL (10 ng/ml plus 1 μg/ml of the enhancer antibody). Hypertrophy was assessed by determining the mRNA levels (by means of RT-PCR) of the atrial natriuretic peptide (ANP), which is a most common molecular marker of hypertrophy. Rasagiline (10 μM/ml) was added to the culture 1 hour before Fas activation and remained in the medium throughout the 24 hours exposure to rFasL. In these preliminary experiments we have found that rasagiline prevented Fas-mediated hypertrophy (data not shown).

Figure 5:
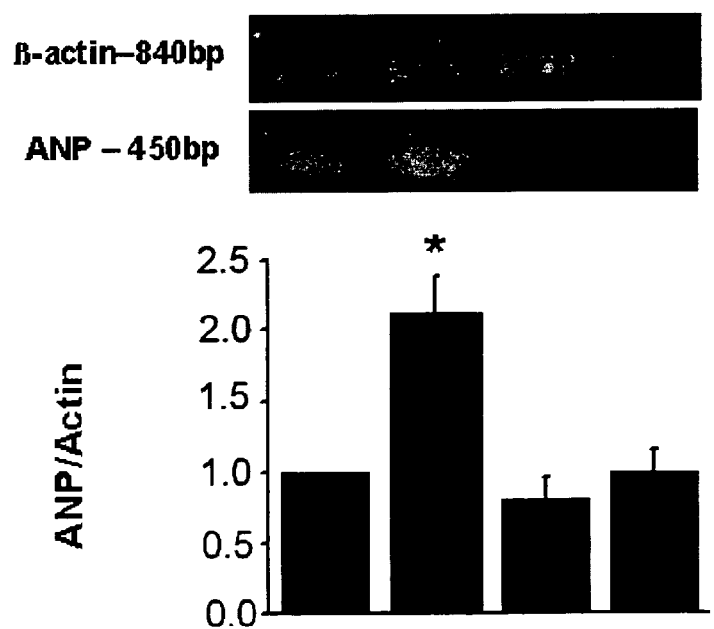
FIG. 5 shows that both propargylamine and S(−)—N-propargyl-1-aminoindan (TVP1022) block Fas-mediated hypertrophy in cultured neonatal rat ventricular myocytes. The top panel depicts representative atrial natriuretic peptide (ANP) mRNA blots in control, rFasL, rFasL+propargylamine, and in rFasL+TVP1022. The lower panel depicts the summary of three experiments performed with each one of these drugs. Hypertrophy was expressed as the ratio between ANP and actin. *P<0.05 vs. control.

In order to test whether S(−)—N-propargyl-1-aminoindan and propargylamine have the same effect on marked hypertrophy induced in cultured neonatal rat ventricular myocytes, similar experiments were performed using either propargylamin or S(−)—N-propargyl-1-aminoindan (both at a concentration of 10 μM) instead of rasagiline. As shown in FIG. 5, the marked ANP mRNA elevation induced by Fas activation for 24 hours was completely blocked by both S(−)—N-propargyl-1-aminoindan and propargylamine (3 experiments per each drug).

Based on these experiments we conclude that rasagiline, S(−)—N-propargyl-1-aminoindan and propargylamine protect ventricular myocytes against hypertrophy caused by activation of the Fas receptor, a finding which may have an important clinical significance.

Example 5

Figure 6A:
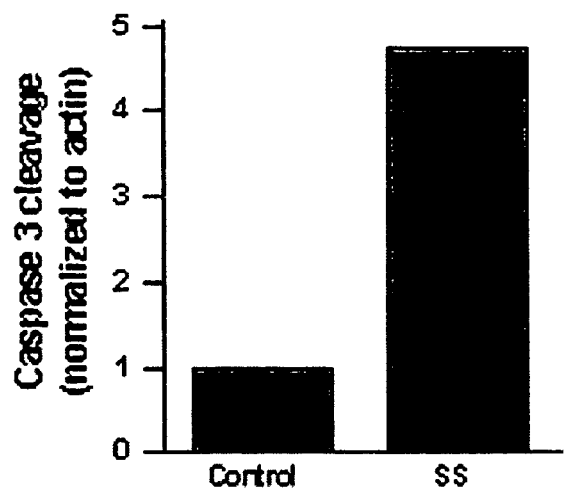
FIGS. 6A-6C show the effect of serum starvation (SS) in cultures of neonatal rat ventricular myocytes (NEVM) on apoptosis induction, indicated by the level of caspase-3 cleavage, and the effect of propargylamine(PA) thereon. (6A) serum starvation causes apoptosis, represented by a marked increase in caspase-3 cleavage. (6B) 0.1 μM propargylamine attenuates serum starvation-induced apoptosis as indicated by decreased level of caspase-3 cleavage (n=3, P<0.01 compared to SS). (6C) 0.1 μM propargylamine attenuates serum starvation-induced apoptosis as indicated by increased expression of Bcl-2 (n=3, P<0.05 compared to SS).

Propargylamine Protects Cultured Neonatal Rat Ventricular Myocytes Against Serum Starvation-Induced Apoptosis Caspase-3 is a protein of the cysteine-aspartic acid protease (caspase) family, known as a key pro-apoptotic protein and therefore as a common marker of apoptosis. It exists as inactive proenzymes that undergo proteolytic processing at conserved aspartic residues to produce 2 subunits, large and small, that dimerize to form the active enzyme. FIG. 6A shows that serum starvation (0% FCS, 24 hours) in cultutres of neonatal rat ventricular myocytes (NRVM) causes apoptosis, represented by a marked increase in caspase-3 cleavage.

Figure 6B:
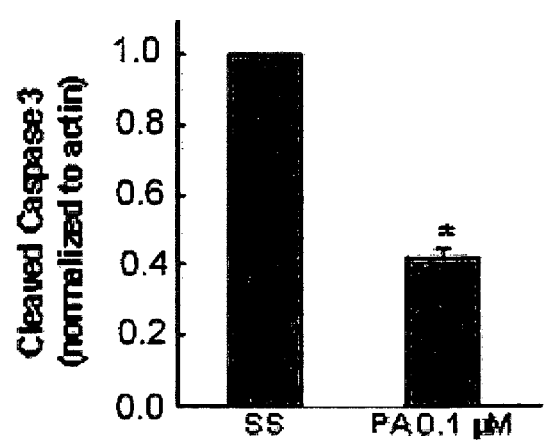
Figure 6C:
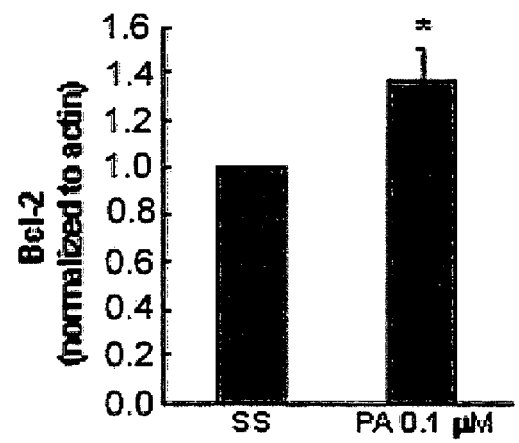

In order to test whether propargylamine can prevent serum starvation-induced apoptosis in cultured neonatal rat ventricular myocytes, we repeated the serum starvation protocol and 0.1 µM propargylamine was introduced to the culture medium 1 hour before serum starvation. As shown in FIGS. 6B-6C, propargylamine attenuated serum starvation-induced apoptosis in neonatal rat ventricular myocytes as indicated both by the drug-induced decrease in caspase 3 cleavage (FIG. 6B) and increase in the expression of mitochondrial Bcl-2, known as an anti-apoptotic protein (FIG. 6C).

Example 6

Propargylamine and S(−)—N-propargyl-1-aminoindan Protect Cultured Neonatal Rat Ventricular Myocytes Against Doxorubicin-Induced Apoptosis Adriamycin (doxorubicin) is a commonly used, highly effective anti cancer drug. However, its clinical efficacy is limited by severe acute cardiotoxic side effects, e.g., apoptosis, that limit the total dose of the medicine that may be used safely. Therefore, finding a drug that will attenuate the cardiotoxic effects of doxorubicin is of prime importance.

In order to test whether propargylamine or S(−)—N-propargyl-1-aminoindan can prevent doxorubicin-induced apoptosis in cultured neonatal rat ventricular myocytes, these drugs (at a concentration of either 1 or 10 µM) were introduced to the culture medium 24 hours before the incubation (24 hours) with 1 µM doxorubicin.

Figure 7:
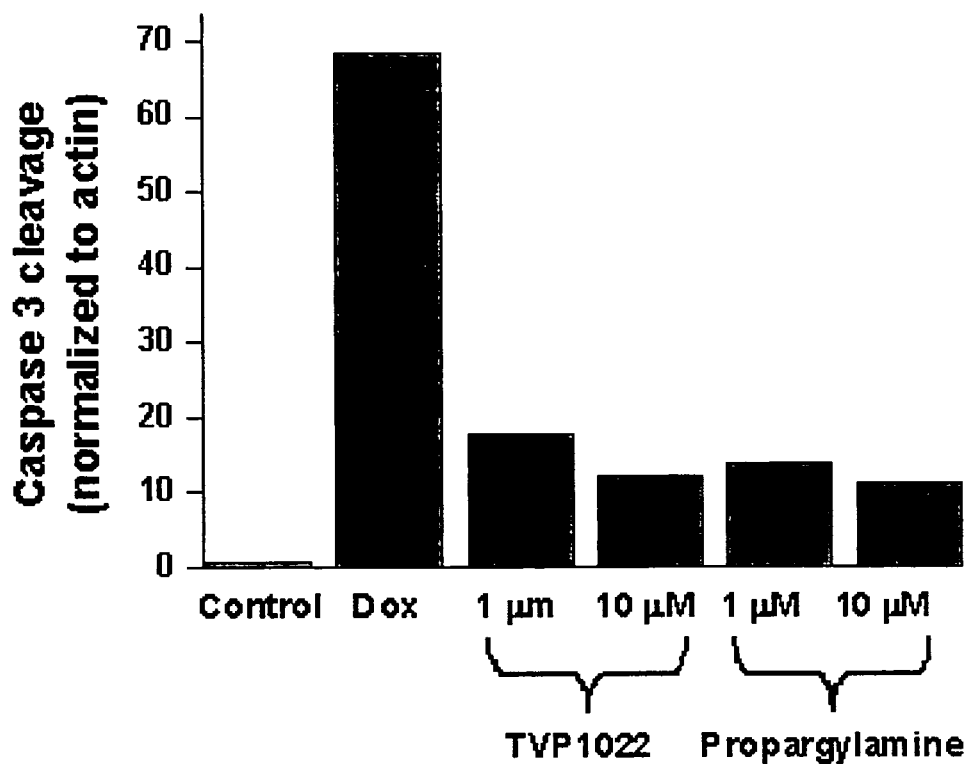
FIG. 7 shows that both S(−)—N-propargyl-1-aminoindan (TVP1022) and propargylamine, at a concentration of either 1 or 10 μM, significantly attenuate the doxorubicin-induced apoptosis effect in cultured neonatal rat ventricular myocytes, as indicated by the drug-induced decrease in caspase-3 cleavage.
Figure 8A:
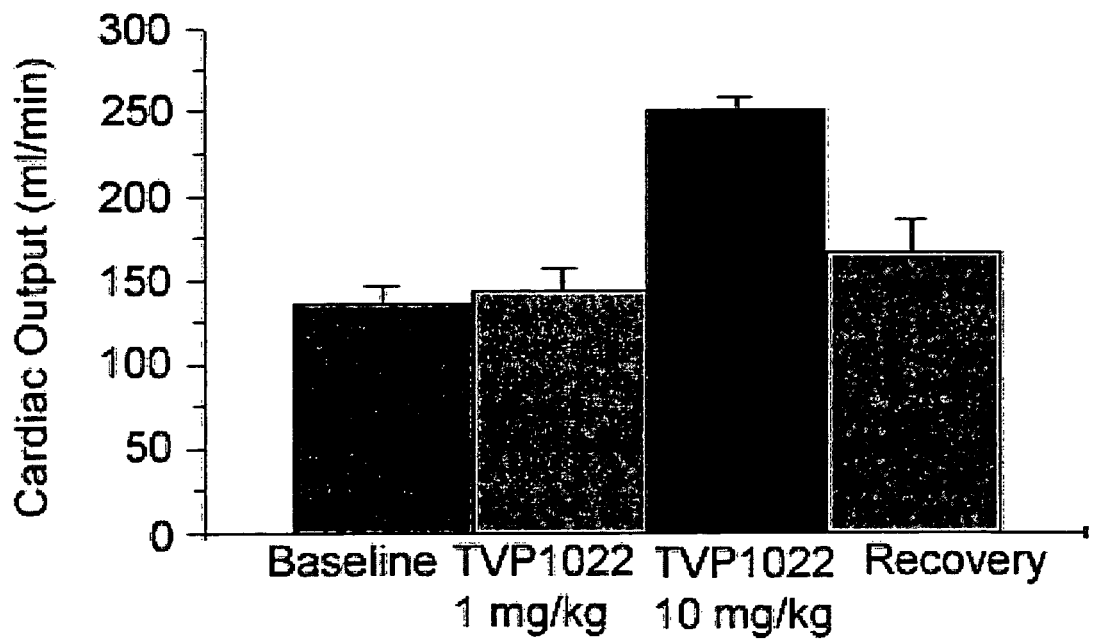
FIGS. 8A-8D show the effect of intravenous administration of S(−)—N-propargyl-1-aminoindan (TVP1022) (either 1 or 10 mg/kg) on the cardiac function in rats: (8A) cardiac output (ml/min); (8B) cardiac index (ml/min * 100 gr body weight); (8C) heart rate (beats/min); and (8D) mean arterial pressure (mm/Hg). Recovery=after washout period.
Figure 8B:
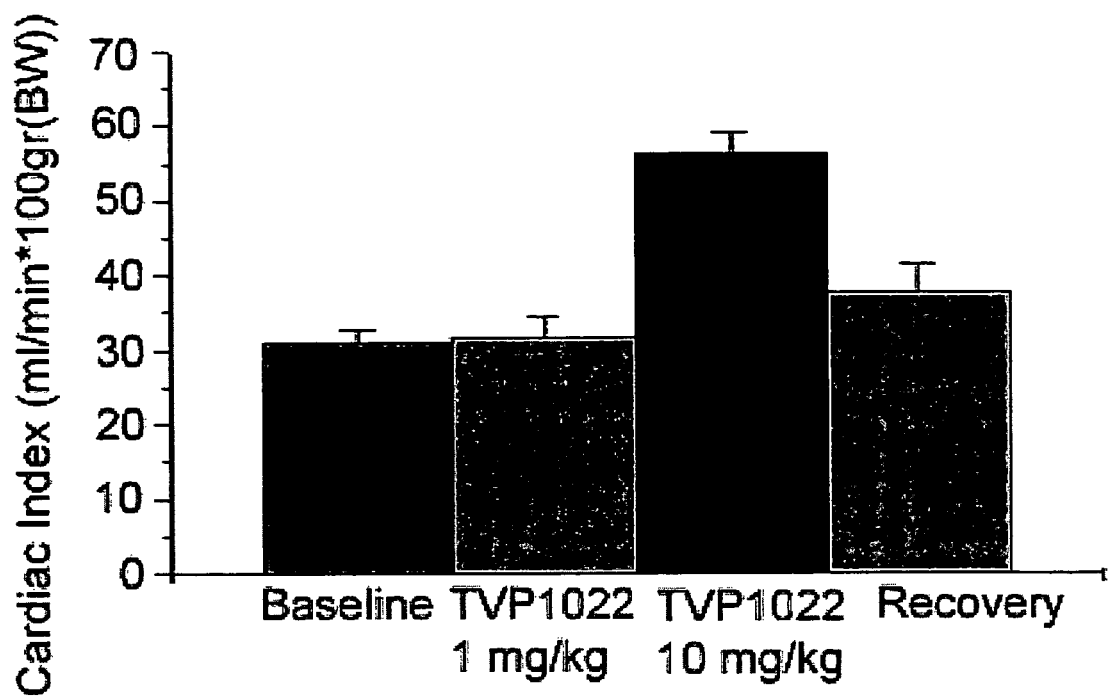
Figure 8C:
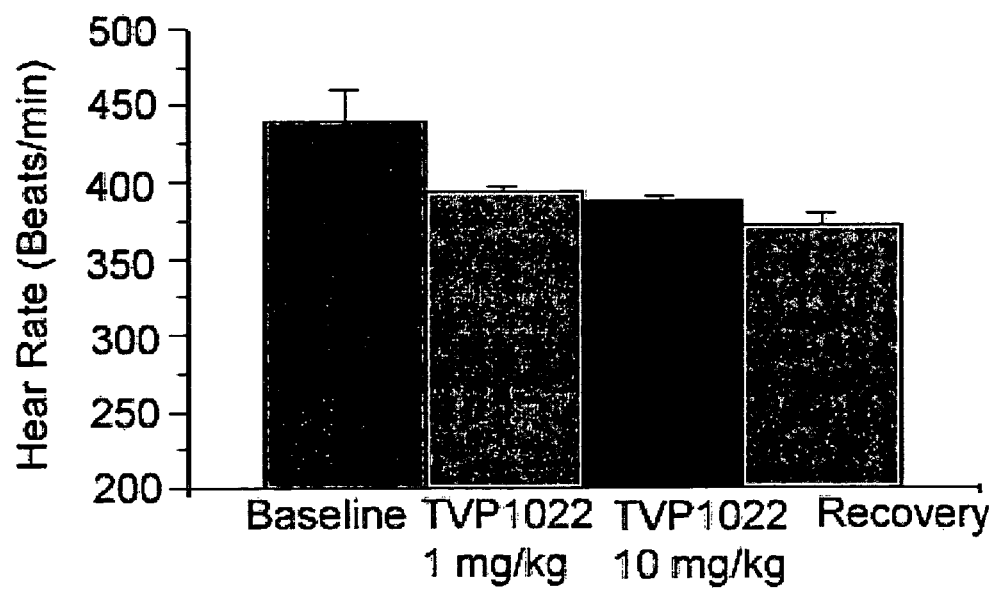
Figure 8D:
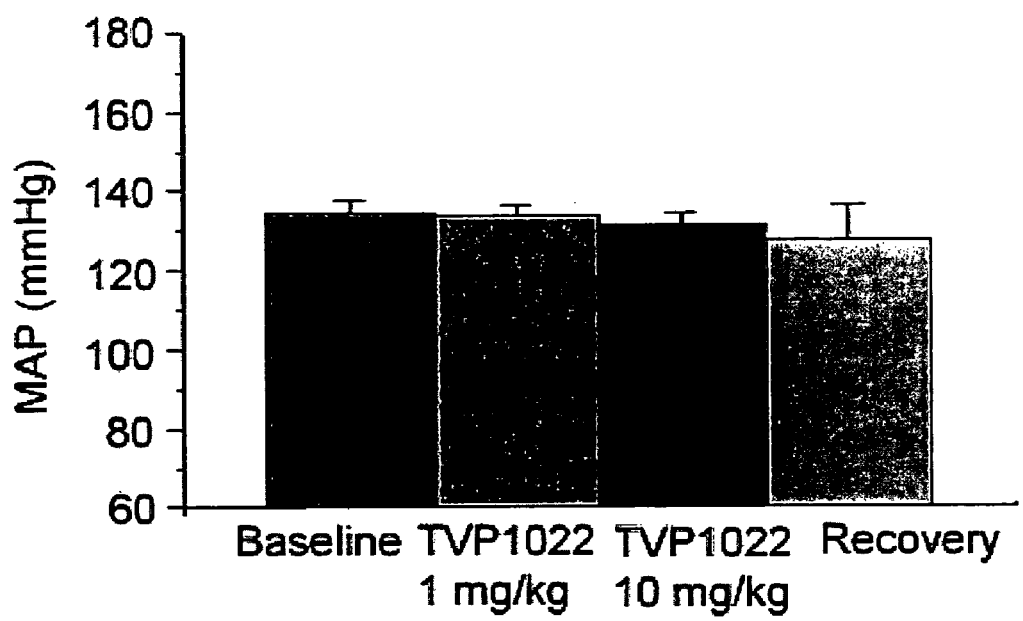

As shown in FIG. 7, doxorubicin (Dox) induced marked apoptosis, as indicated by the marked increase in caspase-3 cleavage, whereas the doxorubicin-induced apoptosis effect was significantly attenuated by propargylamine and S(−)—N-propargyl-1-aminoindan, as indicated by the drug-induced decrease in caspase-3 cleavage.

Example 7

S(−)—N-propargyl-1-aminoindan Improves Cardiac Function

As the first step in testing the beneficial in vivo efficacy of the propargylamine derivatives on the cardiac function, we measured key cardiovascular hemodynamic parameters in control naïve rats, and in rats administered IV with a bolus of 1 mg/kg S(−)—N-propargyl-1-aminoindan, followed with a bolus of 10 mg/kg S(−)—N-propargyl-1-aminoindan (Sprague Dawley rats were used, n=3 rats in each group). Measurements were made at baseline, 30 minutes after each drug administration, and 1 hour (recovery) after drug administration.

As shown in FIGS. 8A-8D, intravenous administration of 10 mg/kg S(−)—N-propargyl-1-aminoindan had prominent beneficial effect on cardiac function. In particular, S(−)—N-propargyl-1-aminoindan markedly increased cardiac output (8A) and cardiac index (8B), but did not affect heart rate (8C) or mean arterial pressure (MAP) (8D). The above-described effect was reversible during the washout period.

Example 8

Propargylamine and S(−)—N-propargyl-1-aminoindan Increase Anti-Apoptotic Proteins in Naïve Rats The major goal of the experiments described in the following Examples was to examine whether pre-treatment with a propargylamine derivative can confer protection against "future" stressful cardiac insults. The clinical implication of this question is whether it will be able to protect patients at risk. In particular, we investigated whether propargylamine and S(−)—N-propargyl-1-aminoindan can attenuate the cardiac dysfunction in rats with congestive heart failure (CHF) caused by volume overload induced by aortocaval fistula (AVF).

In this experiment we tested the effects of propargylamine and S(−)—N-propargyl-1-aminoindan on several key anti-apoptotic and pro-apoptotic proteins in hearts of naïve rats.

Figure 9A:
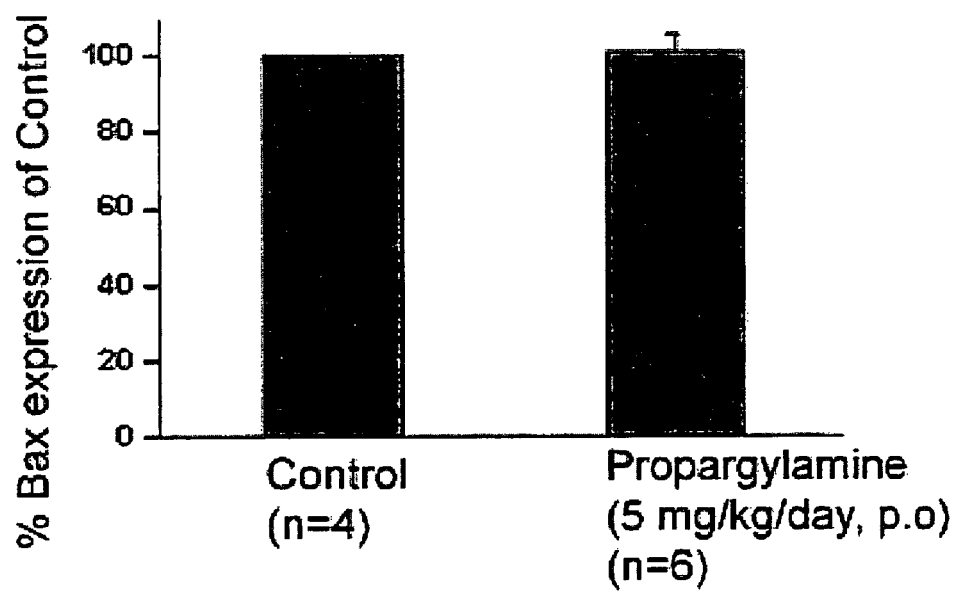
FIGS. 9A-9E show the effects of propargylamine and S(−)—N-propargyl-1-aminoindan (TVP1022) (5 mg/kg/day), orally administered for 21 days, on the expression of mitochondrial Bax, a pro-apoptotic protein, and of mitochondrial Bcl-2 and PKC-ε, both anti-apoptotic proteins. Propargylamine does not affect Bax expression (9A) but increases Bcl-2 expression (9B), resulting in marked increase in the ratio Bcl-2/Bax expression (9C). Propargylamine increases PKC-ε expression (9D). TVP1022 increases PKC-ε expression (9E).
Figure 9B:
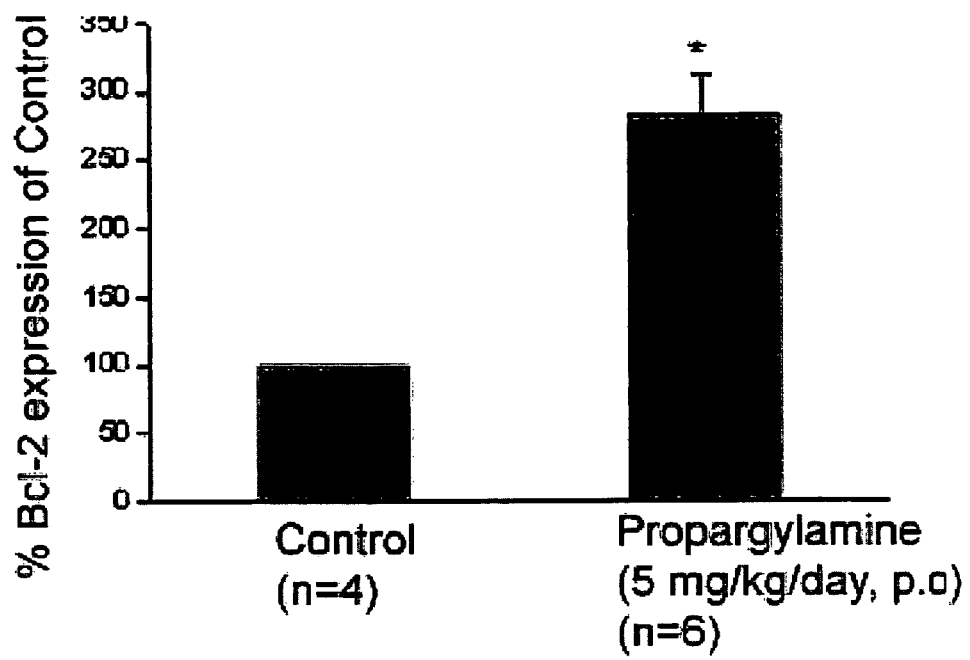
Figure 9C:
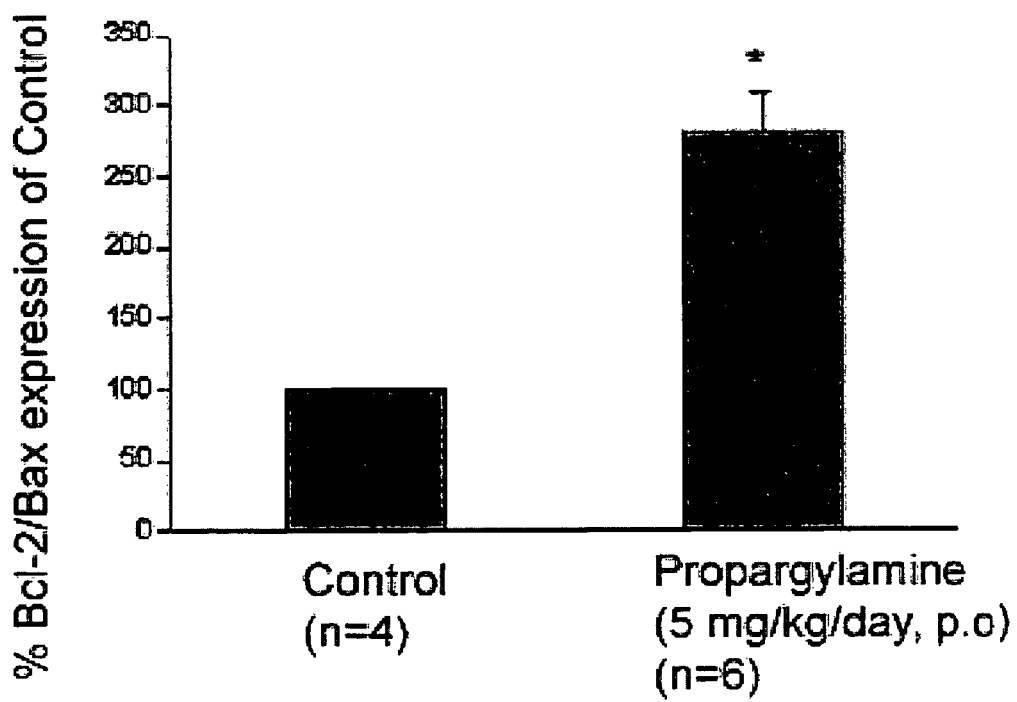
Figure 9D:
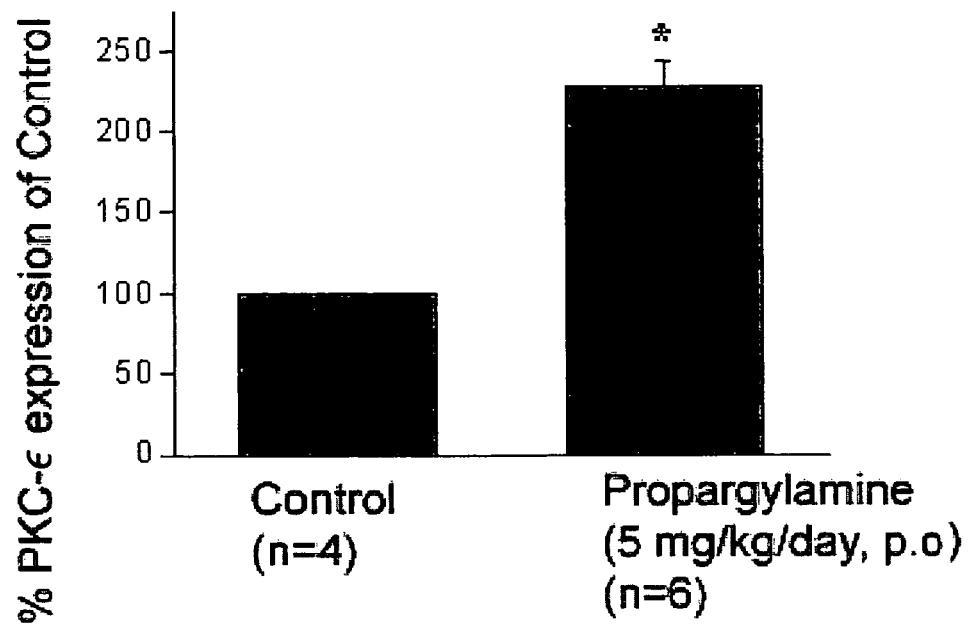
Figure 9E:
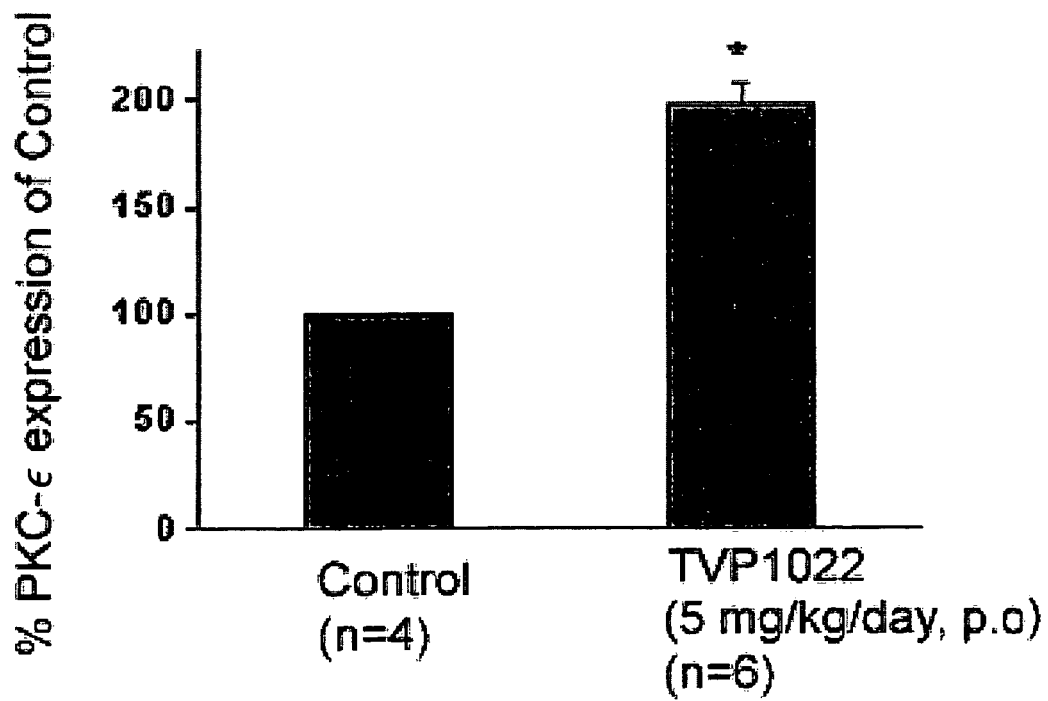

The drugs (5 mg/kg/day) were orally administered to rats for 21 days (n=4-6 rats in each group), and measurements were made after sacrifice. These experiments showed that propargylamine did not affect the expression of mitochondrial pro-apoptotic protein Bax (FIG. 9A), whereas it markedly increased the expression of the mitochondrial anti-apoptotic protein Bcl-2 (FIG. 9B), resulting in marked increase in the ratio Bcl-2/Bax (FIG. 9C), thus generating an anti-apoptotic effect. Furthermore, both propargylamine and S(−)—N-propargyl-1-aminoindan increased the expression of the key anti-apoptotic PKC-ε (FIGS. 9D-9E, respectively).

Example 9

Figure 10A:
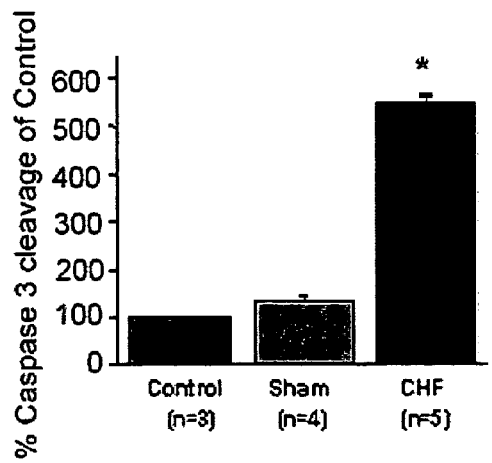
FIGS. 10A-10B show that both caspase-3 (10A) and cytochrome C (10B) markedly increase following induction of volume overload, indicating that volume overload-induced CHF is associated with increased expression of these two proteins. Sham-operated rats served as controls.
Figure 10B:
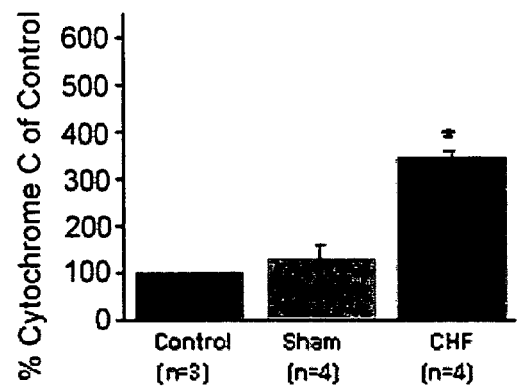

Propargylamine and S(−)—N-propargyl-1-aminoindan Generate an Anti-Apoptotic Effect in CHF Rats Rats were treated as described in Materials and Methods hereinabove and volume overload was induced by surgical creation of an aortocaval fistula (AVF). Sham-operated rats served as controls. 14 days after induction of volume-overload, caspase-3 cleavage and cytosolic cytochrome C, both pro-apoptotic proteins, were analyzed. As shown in FIGS. 10A-10B, both caspase-3 and cytochrome C were markedly increased, indicating that volume overload-induced congestive heart failure (CHF) is associated with increased expression of these two proteins.

Figure 11A:
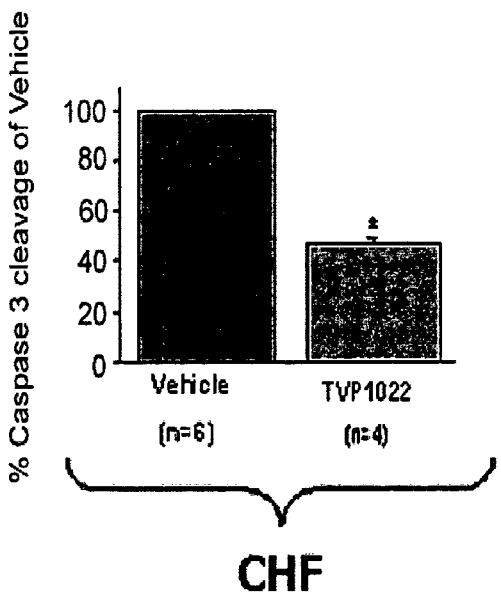
FIGS. 11A-11B show that both S(−)—N-propargyl-1-aminoindan (TVP 1022) and propargylamine significantly reduce CHF-induced increase in caspase-3 and cytosolic cytochrome C, both pro-apoptotic proteins. (11A) Effect of TVP1022 (7.5 mg/kg/day, orally administered for 21 days) on caspase-3 expression in CHF-induced rats (vehicle=untreated CHF rats). (11B) Effect of TVP1022 (1 mg/kg/day) and propargylamine (5 mg/kg/day), orally administered for 21 days, on cytochrome C expression in CHF-induced rats (vehicle=untreated CHF rats).
Figure 11B:
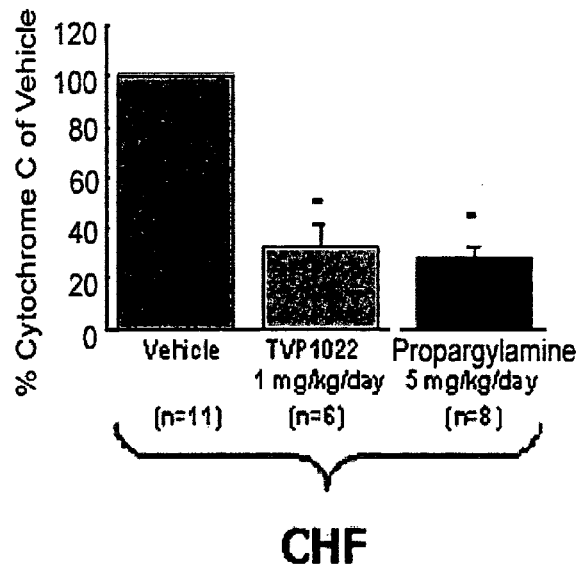

In the following experiment we tested whether propargylamine or S(−)—N-propargyl-1-aminoindan can reduce CHF-induced increase in caspase-3 and cytochrome C. Rats were treated and drugs were administered (1 or 7.5 mg/kg/day S(−)—N-propargyl-1-aminoindan, or 5 mg/kg/day propargylamine) as described in Materials and Methods hereinabove. As shown in FIGS. 11A-11B, both drugs significantly reduced CHF-induced increase in caspase-3 and cytochrome C, suggesting that propargylamine derivatives produce an anti-apoptotic effect both in control and CHF rats, by shifting the balance between the anti-apoptotic proteins and the pro-apoptotic proteins towards the former.

Example 10

Propargylamine and
S(−)—N-propargyl-1-aminoindan Prevent
Ventricular Hypertrophy and the Decline Ventricular
Function in CHF Rats In this set of experiments we determined the ability of pre-treatment with propargylamine or S(−)—N-propargyl-1-aminoindan to prevent ventricular hypertrophy and the decline in ventricular function in CHF rats.

Rats were treated as described in Materials and Methods hereinabove and volume overload was induced by surgical creation of an aortocaval fistula (AVF). Drugs (7.5 mg/kg/day) were administered according to the protocol described above, starting 7 days prior to surgery (day 0) and during 21 days. Cardiac function was determined by echocardiography, from which two principle parameters, namely, diastolic area and systolic area, were calculated. These parameters were used for calculating the fractional shortening, which is an established measure of the ventricular contraction capacity, according to the equation: Fractional shortening =(diastolic area-systolic area)/diastolic area.

Figures 12A, 12B, 12C:
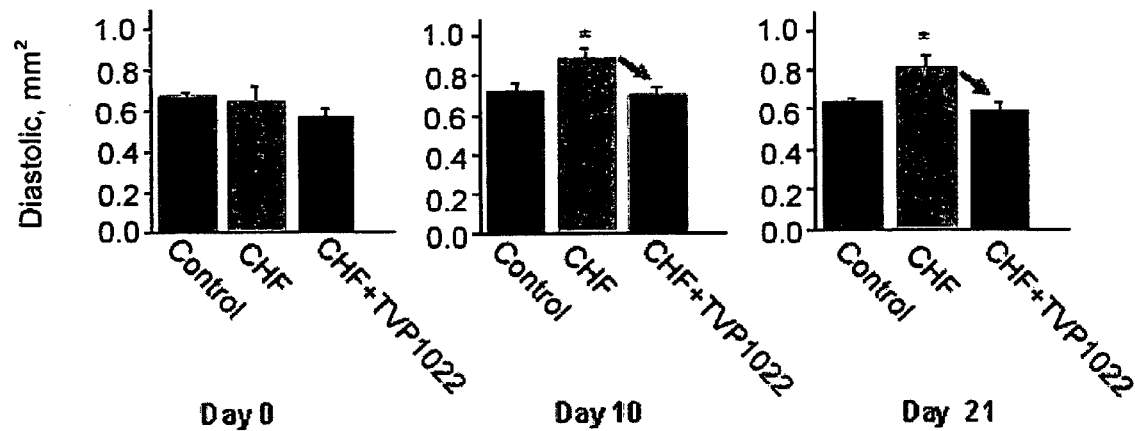
FIGS. 12A-12C show that S(−)—N-propargyl-1-aminoindan (TVP1022) completely prevents the hypertrophic increase in the diastolic area seen in CHF rats at days 10 and 21 of the treatment protocol, as described in Material and Methods hereinafter.
Figures 13A, 13B, 13C:
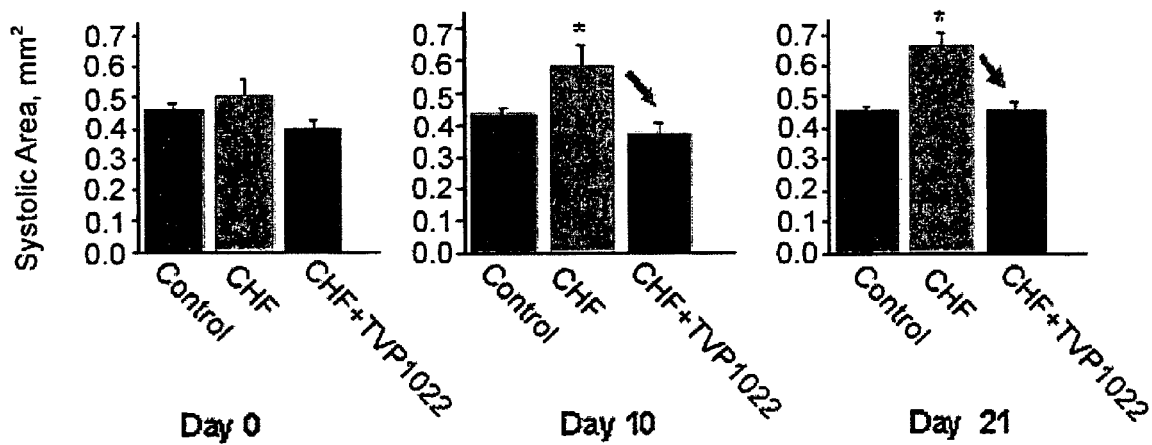
FIGS. 13A-13C show that S(−)—N-propargyl-1-aminoindan (TVP1022) completely prevents the hypertrophic increase in the systolic area seen in CHF rats at days 10 and 21 of the treatment protocol, as described in Material and Methods hereinafter.
Figures 14A, 14B, 14C:
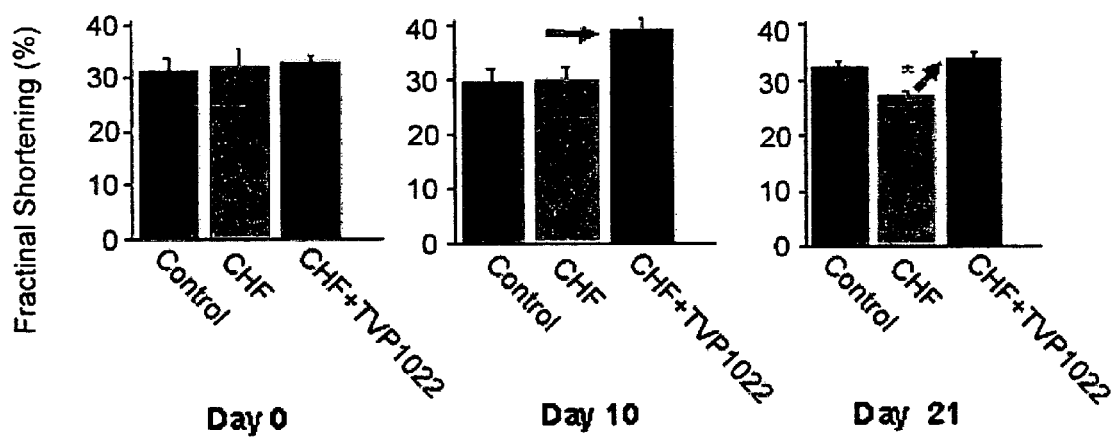
FIGS. 14A-14C show that the fractional shortening in the CHF rats, 14 days post surgical creation of an aorto-caval fistula (AVF), is significantly reduced, but completely prevented by administration of S(−)—N-propargyl-1-aminoindan (TVP1022), as described in Material and Methods hereinafter.

As shown in FIGS. 12 and 13, respectively, the treatment with S(−)—N-propargyl-1-aminoindan completely prevented the hypertrophic increase in the diastolic and systolic areas seen in the CHF group (n=3) at days 10 (3 days post-surgery) and 21 (14 days post-surgery). Furthermore, as shown in FIG. 14, the fractional shortening in the CHF rats on day 21 was significantly reduced compared to the control rats, but S(−)—N-propargyl-1-aminoindan completely prevented this reduction.

Figure 15A:
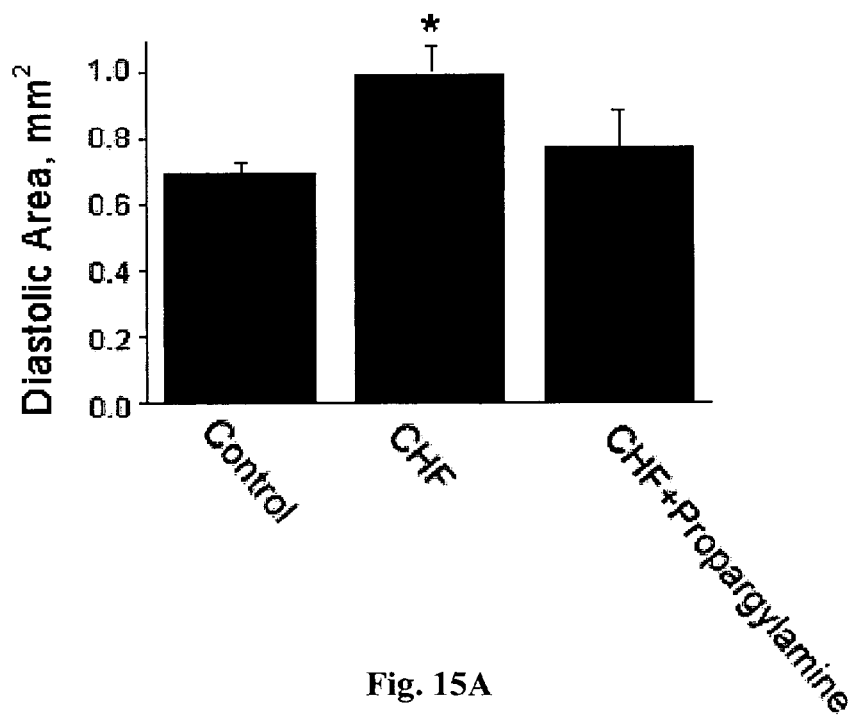
FIGS. 15A-15C show that the administration of propargylamine as described in Material and Methods hereinafter completely prevents the hypertrophic increase in the diastolic (15A) and systolic (15B) areas seen in the CHF rats, 14 days post surgical creation of aortocaval fistula (AVF), as well as a significant reduction in the fractional shortening.
Figure 15B:
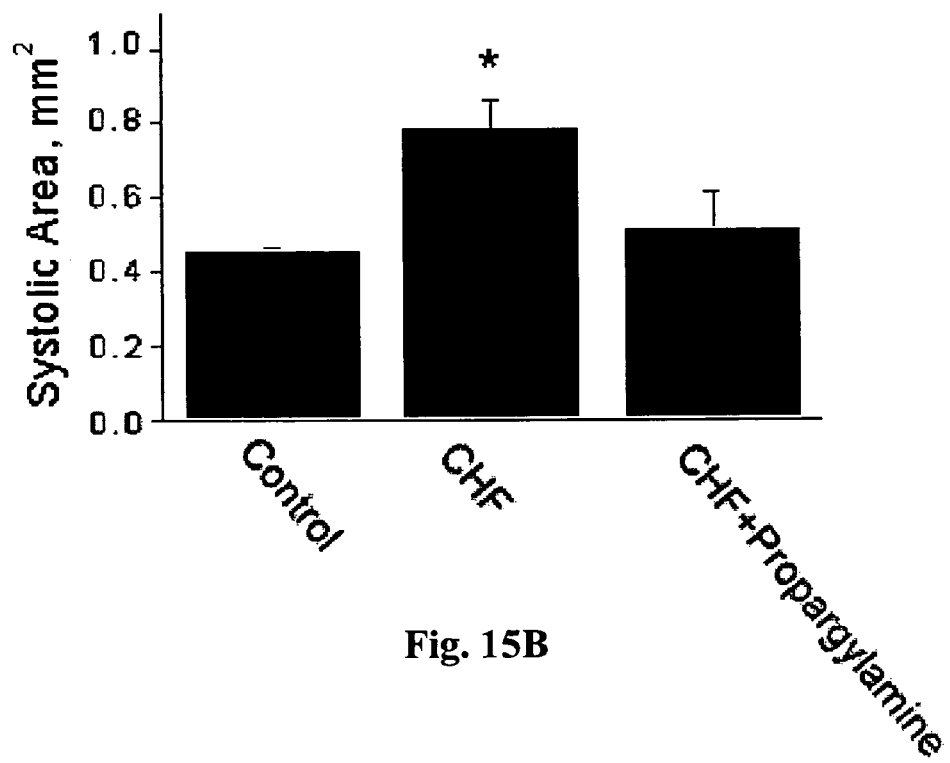
Figure 15C:
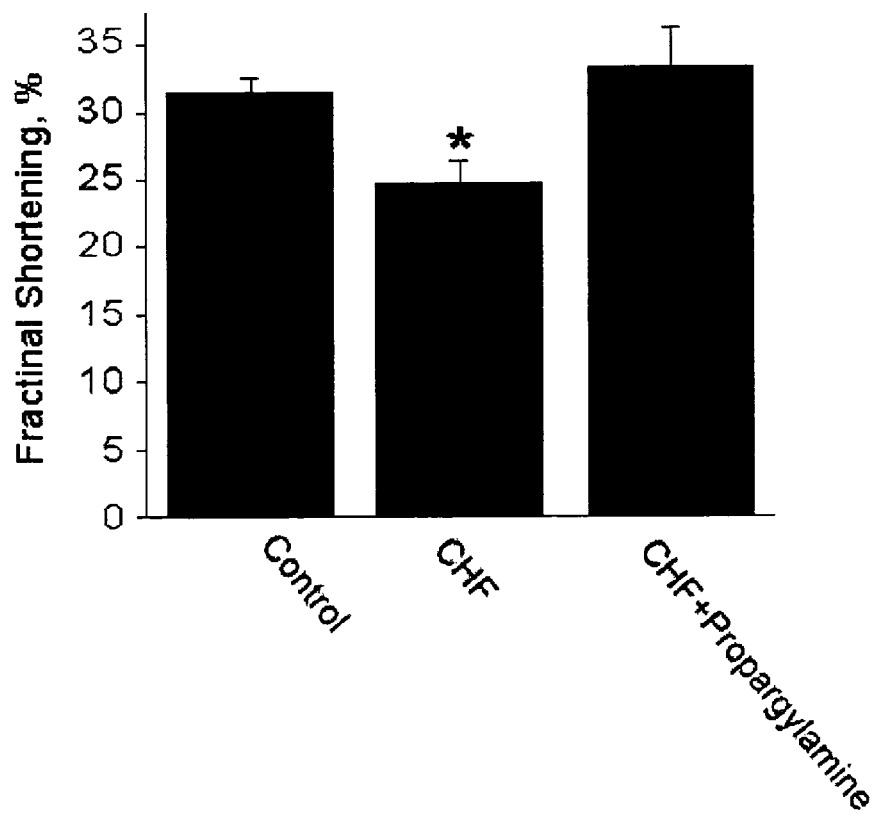

Similar results were obtained with propargylamine using identical experimental and drug administration protocols. As shown in FIGS. 15A-15B, the treatment with propargylamine completely prevented the hypertrophic increase in the diastolic and systolic areas seen in the CHF rats 14 days post-surgery. FIG. 15C shows that the fractional shortening in the CHF rats, 14 days post-surgery was significantly reduced, however, this reduction was completely prevented by the propargylamine.

These in vivo experiments are of prime importance since they demonstrate that both S(−)—N-propargyl-1-aminoindan and propargylamine block the volume-overload induced hypertrophy and the reduction in ventricular mechanical function in CHF rats.

REFERENCES

Abu-Raya, S. Tabakman, R. Blaugrund, E. Trembovler, V. Lazarovici, P., Neuroprotective and neurotoxic effects of monoamine oxidase-B inhibitors and derived metabolites under ischemia in PC12 cells, *Eur. J. Pharmacol.*, 2002, 434, 109-116

Am, O. B. Amit, T. Youdim, M. B. H., Contrasting neuroprotective and neurotoxic actions of respective metabolites of anti-Parkinson drugs rasagiline and selegiline, *Neurosci. Lett.*, 2004, 355, 169-172

Berke, G., The Fas-based mechanism of lymphotoxicity, *Human Immunol.*, 1997, 54, 1-7

Binah, O., Immune effector mechanisms in myocardial pathologies, *Int J Mol Med.*, 2000, 6(1), 3-16

Birkmayer, W. Riederer, P. Ambrozi, L. Youdim, M. B. H., Implications of combined treatment with madopar and 1-deprenyl in Parkinson's disease, *Lancet.*, 1977, 2, 439-443

Brooks, D. J. Sagar, H., UK-irish Entacapone Study Group, Entacapone is beneficial in both fluctuating and non-fluctuating patients with Parkinson's disease: a randomized, placebo controlled, double blind, six month study, *J. Neurol. Neurosurg. Psychiatry*, 2003, 74, 1071-1079

Durden, D. A. Dyck, L. E. Davis, B. A. Liu, Y. D. Boulton, A. A., Metabolism and pharmacokinetics, in the rat, of (R)—N-(2-Heptyl)Methyl-propargylamine(R-2HMP), a new potent monoamine oxidase inhibitor and antiapoptotic agent, *Drug Metab. Dispos.*, 2000, 28(2), 147-154

Finberg, J. P. Ari, G. Lavian, G. Hovevey-Sion, D., Modification of alpha-2 presynaptic receptor activity and catecholamine release following chronic MAO inhibition, *J Neural Transm Suppl.*, 1990, 32, 405-412

Finberg, J. P. M. Lamensdorf, I. Weinstock, M. Schwartz, M. Youdim, M. B. H., Pharmacology of rasagiline (N-propargyl-IR-aminoindan), *Adv. Neurol.*, 1999, 80, 495-501

Finberg, J. P. Youdim, M. B. H., Pharmacological properties of the anti-Parkinson drug rasagiline; modification of endogenous brain amines, reserpine reversal, serotonergic and dopaminergic behaviors, *Neuropharmacology*, 2002, 43, 1110-1118

Fliss, H. Gattinger, D., Apoptosis in ischemic and reperfused rat myocardium, *Circ. Res.*, 1996, 79, 949-956

Gassen, M. Lamensdorf, I. Armony, T. Finberg, J. P. Youdim, M. B. H., Attenuation of methamphetamine induced dopaminergic neurotoxicity by flupirtine: microdialysis study on dopamine release and free radical generation. *J. Neural. Transm.*, 2003, 110, 171-182

Glezer, S. Finberg, J. P., Pharmacological comparison between the actions of methamphetamine and 1-aminoindan stereoisomers on sympathetic nervous function in rat vas deferens, *Eur. J. Pharmacol.*, 2003, 472, 173-177

Haunstetter, A. Izumo, S., Apoptosis: basic mechanisms and implications for cardiovascular disease, *Circ. Res.*, 1998, 82, 1111-1129

Hershkowitz, A. Wolfgram, L. J. Rose, N. R. et al., Coxsackievirus B3 murine myocarditis: a pathologic spectrum of myocarditis in genetically defined inbred strains, *J Am Coll Cardiol*, 1987, 9, 1311-1319

Jeremias, I. Kupatt, C. Villalba-Martin et al., Involvement of CD95/Apo-1/Fas in cell death after myocardial ischemia, *Circulation*, 2000, 102, 915-920

Kraemer, T. Maurer, H. H., Toxicokinetics of amphetamines: metabolism and toxicokinetic data of designer drugs, amphetamine, methamphetamine, and their N-alkyl derivatives. *Ther. Drug. Monit.*, 2002, 24, 277-289

Lavian, G. Finberg, J. P. Youdim, M. B. H., The advent of a new generation of monoamine oxidase inhibitor antidepressants: pharmacologic studies with moclobemide and brofaromine, *Clin. Neuropharmacol.*, 1993, 16 (Suppl. 2), S1-7

Lees, A. J., Comparison of therapeutic effects and mortality data of levodopa and levodopa combined with selegiline in patients with early, mild Parkinson's disease. Parkinson Disease Research Group of the United Kingdom, *Br. Med. J.*, 1995, 311, 1601-1607

Mandel, S. Grunblatt, E. Riederer, P. Gerlach, M. Levites, Y. Youdim, M. B. H., Neuroprotective strategies in Parkinson's disease: an update on progress, *CNS. Drugs.*, 2003, 17, 729-762

Parkinson Study Group (Datatop), Selegiline and Parkinson's disease. *N. Engl. J. Med.,* 1989, 321, 1364-1371

Parkinson Study Group, A controlled trial of rasagiline in early Parkinson disease: the TEMPO Study. *Arch. Neurol.,* 2002, 59, 1937-1943

Reynolds, G. P. Riederer, P. Sandler, N. R. Jellinger, K. Seemali, D., Amphetamine and 2-phenylethylamine in post mortem Parkinson brains after 1-deprenyl administration, *J. Neural. Transm.,* 1978, 43, 271-278

Riederer, P. Rinne, U. K., Selegiline in Parkinson's disease: An update, *Mov. Disords.,* 1992, 8 (Suppl. 1), 51-54

Shin, H. S., Metabolism of selegiline in humans: Identification, excretion and stereochemistry of urine metabolites, *Drug. Metab. Dispos.,* 1997, 25, 657-662

Simpson, L. L., Evidence that deprenyl, a type B monoamine oxidase inhibitor is an indirectly acting sympathomimetic amine, *Biochem. Pharmacol.,* 1978, 27, 1591-1595

Szoko, E. Kalasz, H. Magyat, K., Biotransformation of deprenyl enantiomers, *Eur. J. Drug. Metab. Pharmacokinet.,* 1999, 24, 315-319

Tatton, W. G., Selegiline can mediate neuronal rescue rather than neuronal protection. *Movement Disorders* 8 (Supp. 1), 1993, S20-S30

Tatton W. G. Greenwood, C. E., Rescue of dying neurons: a new action for deprenyl in MPTP parkinsonism, *J. Neurosci. Res.,* 1991, 30(4), 666-672

Yamaguchi, S. Yamaoka, M. Okuyama, M. Nitoube, J. Fukui, A. Shirakabe, M. Shirakawa, K. Nakamura, N. Tomoike, H., Elevated circulation levels and cardiac secretion of soluble Fas ligand in patients with congestive heart failure, *Am. J. Cardiol.,* 1999, 83, 1500-1503

Yaniv, G. Shilkrut, M. Lotan, R. Larish, S. Berke, G. Binah, O., Hypoxia predisposes neonatal rat ventricular myocytes to apoptosis induced by activation of the Fas (CD95/Apo-1) receptor: Fas activation and apoptosis in hypoxic myocytes, *Cardiovasc Res,* 2002, 54, 611-623

Yaoita, H. Ogawa, K. Macehara, K. Maruyama, Y., Attenuation of ischemia/reperfusion injury in rats by a caspase inhibitor, *Circulation,* 1998, 97, 276-281

Youdim, M. B. H. Gross, A. Finberg, J. P., Rasagiline [N-propargyl-1R(+)-aminoindan], a selective and potent inhibitor of mitochondrial monoamine oxidase B, *Br. J. Pharmacol.,* 2001, 132, 500-506

Youdim, M. B. H., Rasagiline: an antiparkinson drug with neutroprotective activity, *Expert. Rev., Neurotherapeutics,* 2003, 3, 737-749

Zimmermann, K. Waldmeier, P. C. Tatton, W. G., Dibenzoxepines as treatments for neurodegenerative diseases, *Pure Appl Chem,* 1999, 71(11), 2039-2046

The invention claimed is:

1. A method for reducing apoptosis resulting from myocardial infarction in a subject in need thereof, said method comprising administering to the subject an effective amount of S(-)—N-propargyl-1-aminoindan or a pharmaceutically acceptable salt thereof.

2. The method of claim 1, wherein S(-)—N-propargyl-1-aminoindan is administered.

3. The method of claim 1, wherein said pharmaceutically acceptable salt of S(-)—N-propargyl-1-aminoindan is administered.

4. The method of claim 3, wherein said pharmaceutically acceptable salt is selected from the group consisting of the mesylate salt; the esylate salt; the sulfate salt; the hydrochloride salt the maleate salt; the fumarate salt; the tartrate salt; the hydrobromide salt; the p-toluenesulfonate salt; the benzoate salt; the acetate salt; and the phosphate salt of S(-)—N-propargyl-1-aminoindan.

5. A method for reducing apoptosis and cardiac myocyte cell death following onset and as a result of myocardial infarction in a patient in need thereof, said method comprising administering to the subject an effective amount of S(-)—N-propargyl-1-aminoindan or a pharmaceutically acceptable salt thereof.

* * * * *